United States Patent
Dossett et al.

(10) Patent No.: US 10,342,621 B2
(45) Date of Patent: Jul. 9, 2019

(54) METHODS FOR FACILITATING INDIVIDUALIZED KINEMATICALLY ALIGNED KNEE REPLACEMENTS AND DEVICES THEREOF

(71) Applicant: iTKR Software LLC, Scottsdale, AZ (US)

(72) Inventors: Robert Alan Dossett, Milford, MA (US); Harold Gene Dossett, Scottsdale, AZ (US)

(73) Assignee: ITKR Software LLC, Scottsdale, AZ (US)

(*) Notice: Subject to any disclaimer, the term of this patent is extended or adjusted under 35 U.S.C. 154(b) by 224 days.

(21) Appl. No.: 15/351,667

(22) Filed: Nov. 15, 2016

(65) Prior Publication Data

US 2017/0065350 A1    Mar. 9, 2017

Related U.S. Application Data

(63) Continuation of application No. 14/932,653, filed on Nov. 4, 2015, now Pat. No. 9,532,845.

(Continued)

(51) Int. Cl.
*A61B 34/10* (2016.01)
*G16H 50/50* (2018.01)
(Continued)

(52) U.S. Cl.
CPC .............. *A61B 34/10* (2016.02); *A61B 34/25* (2016.02); *G16H 20/40* (2018.01); *G16H 50/50* (2018.01);
(Continued)

(58) Field of Classification Search
CPC ........ A61B 34/10; A61B 34/25; G16H 50/50; G06F 19/00
See application file for complete search history.

(56) References Cited

U.S. PATENT DOCUMENTS 5,682,886 A * 11/1997 Delp .................... A61B 17/154
128/920
5,871,018 A * 2/1999 Delp .................... A61B 17/154
128/898

(Continued)

FOREIGN PATENT DOCUMENTS

EP        3395281 A1    10/2018
WO    2006089069 A2     8/2006
(Continued)

OTHER PUBLICATIONS

Luo, "Reference Axes for Reconstruction of the Knee", Mar. 1, 2004, pp. 251-257, Elsevier B.V.

(Continued)

*Primary Examiner* — Zade Coley
(74) *Attorney, Agent, or Firm* — Pepper Hamilton LLP

(57) ABSTRACT

Methods, non-transitory computer readable media, and individualized kinematic knee replacement analysis computing devices that obtains prosthesis data for a selected prosthesis. Anatomical and pathoanatomical data for a specific patient is generated. The anatomical data comprises at least a coronal mechanical lateral distal femoral angle that is specific to the patient. Bone and cartilage resection data is generated based at least in part on the prosthesis data, the anatomical data, and the pathoanatomical data. A recommended three-dimensional knee replacement surgeon plan for the patient, comprising the bone and cartilage resection data for facilitating implantation of the prosthesis in the patient, is output.

12 Claims, 16 Drawing Sheets

Related U.S. Application Data

(60) Provisional application No. 62/203,738, filed on Aug. 11, 2015.

(51) Int. Cl.
    *A61B 34/00* (2016.01)
    *G16H 20/40* (2018.01)
    *A61B 17/17* (2006.01)
    *A61B 17/15* (2006.01)
    *A61B 17/56* (2006.01)

(52) U.S. Cl.
    CPC ........... *A61B 17/155* (2013.01); *A61B 17/157* (2013.01); *A61B 17/1764* (2013.01); *A61B 2017/568* (2013.01); *A61B 2034/102* (2016.02); *A61B 2034/105* (2016.02); *A61B 2034/107* (2016.02); *A61B 2034/108* (2016.02); *A61B 2034/252* (2016.02); *A61B 2034/256* (2016.02)

(56) References Cited

U.S. PATENT DOCUMENTS

| | | | |
|---|---|---|---|
| 7,388,972 B2* | 6/2008 | Kitson | A61F 2/30942 382/128 |
| 8,265,949 B2* | 9/2012 | Haddad | A61B 17/157 705/2 |
| 8,473,305 B2* | 6/2013 | Belcher | G06F 19/00 705/2 |
| 8,532,807 B2* | 9/2013 | Metzger | A61F 2/46 700/98 |
| 9,901,463 B2 | 2/2018 | Mahfouz | |
| 2004/0068187 A1* | 4/2004 | Krause | A61B 17/15 600/443 |
| 2005/0054917 A1* | 3/2005 | Kitson | A61F 2/30942 600/427 |
| 2006/0015120 A1* | 1/2006 | Richard | A61B 90/06 606/102 |
| 2007/0173815 A1* | 7/2007 | Murase | A61B 17/15 606/53 |
| 2009/0089081 A1* | 4/2009 | Haddad | A61B 17/157 705/2 |
| 2009/0254367 A1* | 10/2009 | Belcher | G06F 19/00 705/2 |
| 2010/0191088 A1* | 7/2010 | Anderson | A61B 17/7074 600/373 |
| 2012/0310399 A1* | 12/2012 | Metzger | A61F 2/46 700/98 |
| 2013/0006661 A1* | 1/2013 | Haddad | A61B 17/157 705/2 |
| 2013/0144135 A1 | 6/2013 | Mahfouz et al. | |
| 2013/0190767 A1* | 7/2013 | Park | A61B 17/154 606/87 |
| 2013/0332128 A1* | 12/2013 | Miles | A61B 34/10 703/6 |
| 2014/0018948 A1* | 1/2014 | Metzger | A61F 2/46 700/98 |
| 2014/0081659 A1* | 3/2014 | Nawana | G16H 50/20 705/3 |
| 2015/0182131 A1 | 6/2015 | Mahfouz et al. | |
| 2016/0008143 A1 | 1/2016 | Mahfouz | |
| 2016/0157751 A1 | 6/2016 | Mahfouz | |
| 2017/0143494 A1 | 5/2017 | Mahfouz | |
| 2017/0340447 A1 | 11/2017 | Mahfouz | |
| 2017/0367766 A1 | 12/2017 | Mahfouz | |
| 2018/0049807 A1 | 2/2018 | Mahfouz | |
| 2018/0055644 A1 | 3/2018 | Mahfouz | |
| 2018/0055655 A1 | 3/2018 | Mahfouz | |
| 2018/0059204 A1 | 3/2018 | Mahfouz | |

FOREIGN PATENT DOCUMENTS

| | | |
|---|---|---|
| WO | 2006089069 A3 | 8/2006 |
| WO | 2010115086 A1 | 10/2010 |
| WO | 2012018851 A1 | 2/2012 |
| WO | 2012048020 A1 | 4/2012 |
| WO | 2015089118 A1 | 6/2015 |
| WO | 2015089118 A9 | 8/2015 |
| WO | 2015160852 A1 | 10/2015 |
| WO | 2016007936 A2 | 1/2016 |
| WO | 2016007936 A3 | 3/2016 |
| WO | 2016201078 A2 | 12/2016 |
| WO | 2017106580 A1 | 6/2017 |
| WO | 2017106794 A1 | 6/2017 |
| WO | 2017151683 A1 | 9/2017 |
| WO | 2017160889 A1 | 9/2017 |
| WO | 2018236936 A1 | 12/2018 |

OTHER PUBLICATIONS

Cherian et al., "Mechanical, Anatomical, and Kinematic Axis in TKA: Concepts and Practical Applications", Mar. 27, 2014, pp. 89-95, Springer.

European Search Report for corresponding European Patent Application Serial No. 16835749.9, 21 Feb. 21, 2019, 1 page.

* cited by examiner

| Variable Name | Question |
|---|---|
| | Preference Data |
| SP-ProsthesisManufacturer | Choose prosthesis manufacturer |
| SP-ProsthesisType | Choose prosthesis type |
| SP-UseManufacturerRecSlope | Use the manufacturers recommended slope? |
| SP-SetLimitCoronalFemoralValgus | Limit coronal femoral implant valgus to maximum number? |
| SP-CoronalFemoralValgusMax | What is the coronal femoral implant valgus limit? |
| SP-DefineCoronalDegreeToMMTranslation | What is the translation of femoral coronal angle degrees to millimeters? (1 degree = ? mm) |
| SP-SetLimitExternalFemoralRotation | Limit femoral external rotation to maximum? |
| SP-ExternalFemoralRotationMax | What is the femoral external rotation maximum? |
| SP-DefineExtRotationDegreeToMMTranslation | What is the translation of femoral external rotation angle degrees to millimeters? (1 degree = ? mm) |
| SP-CoronalTibiaVarusMax | Maximum angle of coronal tibial implant varus? |
| SP-CartilageThickness | What is default cartilage thickness (mm)? |
| SP-AdjustManufacturerDistalFemoralThickness | Adjust manufacturer's thickness of the distal prosthesis for femoral cut planning? |
| SP-DistalFemoralThicknessAdjustment | What is the distal prosthesis thickness adjustment? |
| SP-FlexFemoralComponent | Flex the femoral component? |
| SP-FlexFemoralComponentAmount | What is the amount (in degrees) to flex the femoral component? |

FIG. 6A

| Variable Name | 602 Question |
|---|---|
| | Preference Data |
| SP-AlignProsthesisToPosteriorCondylarAxis | Align femoral rotation with posterior condylar axis (If no, use mechanical alignment: stop) |
| SP-AdditionalPosteriorMedialResection | Add additional resection to the medial posterior cut (to avoid accidentally internally rotating femur)? |
| SP-AdditionalPosteriorMedialResectionAmount | What is the amount of additional posterior medial resection? |
| SP-TibiaCutMax | What is the maximum planned tibial cut thickness? |
| SP-AddPosteriorMedialResectionModerateOrSeverePFSublux | Add additional resection to posterior medial cut for moderate or severe patellofemoral subluxation? |
| SP-AddPosteriorMedialResectionModeratePFSubluxAmount | What is the amount (in mm) of additional resection for moderate patellofemoral subluxation? |
| SP-AddPosteriorMedialResectionSeverePFSubluxAmount | What is the amount (in mm) of additional resection for severe patellofemoral subluxation? |
| SP-AddCorrectionLateralTibialTubercle | Add correction for lateral tibial tubercle? |
| SP-AddCorrectionLateralTibialTubercleAmount | What is the amount of correction for lateral tibial tubercle? |
| SP-CorrectLimbVarus | Make correction for limb varus? |
| SP-LimbVarusCorrectionThreshold | What is the threshold (in degrees) for correcting limb varus? |
| SP-LimbVarusCorrectionAmount | What is the amount (in degrees) of limb varus correction? |
| SP-CorrectLimbValgus | Make correction for limb valgus? |
| SP-LimbValgusCorrectionThreshold | What is the threshold (in degrees) for correcting limb valgus? |
| SP-LimbValgusCoronalCorrectionAmount | What is the amount (in degrees) of limb valgus coronal correction? |
| SP-LimbValgusAxialCorrectionAmount | What is the amount (in degrees) of limb valgus axial correction? |
| SP-PosteriorStabilizedComponent | Use a posterior stabilized component instead of CR component? |
| SP-Kerf | Amount of kerf for each saw cut (in mm)? |

FIG. 6B

| Variable Name | 700 | Question |
|---|---|---|
| | | Observed Data |
| MD-MedialFemoralCartilageWear | | How much medial wear is present? (0%, 25%, 50%, 75% or 100%) |
| MD-LateralFemoralCartilageWear | | How much lateral wear is present? (0%, 25%, 50%, 75% or 100%) |
| MD-PatellofemoralSubluxation | | Is there patellofemoral subluxation? (None, Moderate, Severe) |
| MD-MedialFemoralCondyleWear | | Is there medial femoral condyle bone wear on the coronal view? (0, 1mm, 2mm, 3mm, 4mm) |
| MD-LateralFemoralCondyleWear | | Is there medial lateral condyle bone wear on the coronal view? (0, 1mm, 2mm, 3mm, 4mm) |

FIG. 7

| Variable Name | 800 | Question |
|---|---|---|
| | | Template Data |
| X-LeftOrRight | | Left or right knee? |
| X-MechanicalAnatomicalFemurAngle | | Mechanical angle – Anatomical angle of femur? |
| X-LimbAlignment | | Limb alignment (coronal hip-knee-ankle angle)? |
| X-VarusOrValgus | | Is limb varus or valgus? |
| X-mLDFA | | Mechanical lateral distal femoral angle from long leg coronal view? |
| X-MedialTibialCutThickness | | What is the medial tibial cut thickness (mm)? |
| X-LateralTibialCutThickness | | What is the lateral tibial cut thickness (mm)? |
| X-PatellaThickness | | What is the patella thickness (mm)? |
| X-LateralTibialTubercle | | Is there a lateral tibial tubercle - from 3D imaging? |
| X-TibialSlope | | What is the tibial slope? |

FIG. 8

| Surgeon Plan | | |
|---|---|---|
| Distal femur | 900 | |
| Flexion (degrees) PL-FemoralSagittalFlexionAngle | | 2.0 |
| Valgus angle off Anat. Axis (degrees) PL-FemoralValgusAngleRelToAnatAxis | | 4.0 |
| Valgus angle off Mech Axis (degrees) PL-FemoralValgusAngleRelToMechAxis | | 0.5 |
| | Medial (mm) PL-FemoralMedialDistalResection | 7.5 |
| | Lateral (mm) PL-FemoralLateralDistalResection | 9.5 |
| Posterior Femur | | |
| External rotation angle (degrees) PL-FemoralExternalRotation | | 0.5 |
| | Medial (mm) PL-FemoralPosteriorMedialResection | 9.0 |
| | Lateral (mm) PL-FemoralPosteriorLateralResection | 9.5 |
| Tibia | | |
| Varus angle (off Mech Axis) PL-TibialVarusAngle | | 1.5 |
| | Slope (degrees) PL-TibialSlope | 7.0 |
| | Medial (mm) PL-TibialMedialResection | 4.0 |
| | Lateral (mm) PL-TibialLateralResection | 8.0 |
| Special Considerations | | |
| Possible release needed? PL-PossibleRelease | | No |
| Consider narrow component? PL-ConsiderNarrowComponent | | No |
| May require additional 2 degree ER? PL-ConsiderAddlTwoDegreeExtRotation | | No |
| Posterior Stabilized Implant? SP-PosteriorStabilizedComponent | | No |

FIG. 9

METHODS FOR FACILITATING INDIVIDUALIZED KINEMATICALLY ALIGNED KNEE REPLACEMENTS AND DEVICES THEREOF

This application is a continuation of U.S. patent application Ser. No. 14/932,653, filed on Nov. 4, 2015, which claims the benefit of U.S. Provisional Patent Application Ser. No. 62/203,738, filed on Aug. 11, 2015, each of which is hereby incorporated by reference in its entirety.

FIELD

This technology relates to knee replacements and, more particularly, to methods and devices for facilitating individualized kinematically aligned knee replacements.

BACKGROUND

The ideal alignment for a knee replacement provides the highest possible patient reported outcomes while maintaining durability of these results over time. Currently, mechanical alignment is a standard alignment method used to align knee replacements. This alignment method places the femoral and tibial components at right angles to the femoral and tibial mechanical axes, and attempts to align the limb to a straight line. However, concepts of the optimal alignment of a knee replacement are evolving based on recent science regarding the anatomy and pathoanatomy of the knee, as well as newer clinical information.

For example, mechanically aligned patients with varus preoperative limb deformities show higher outcome scores if the limb remains in some varus after knee replacement. More generally, patients who have a knee replacement with the goal of re-establishing the three kinematic axes of the knee have higher clinical outcome scores than the patients who have knee replacements according to a mechanical alignment. Studies have shown up to 25% of patients are not satisfied with the results of the mechanically aligned knee replacement.

A relatively new technique, referred to as kinematic alignment, attempts to recreate the three kinematic axes of the knee. A randomized double blind controlled trial showed significantly better two-year clinical results with a kinematic alignment technique. In a kinematically aligned knee replacement, each knee is aligned to the patient's own individual anatomy, and there is no limit to the deviation of the implant or limb from the mechanical axis. Generating the resections necessarily to implement a kinematic alignment for a patient is relatively complex and can result in resections and/or alignments that are outside of preferred and/or accepted limits, as well as surgeon errors, leading to reduced outcomes for patients. In response to perceived limitations of mechanical and kinematic alignment, surgeons have been modifying kinematic and mechanical alignment techniques, requiring maintenance of an increasing number of variables to optimally align each knee.

SUMMARY

A method for facilitating individualized kinematically aligned knee replacements includes obtaining prosthesis data for a selected prosthesis. Anatomical and pathoanatomical data for a specific patient is generated. The anatomical data comprises at least a coronal mechanical lateral distal femoral angle that is specific to the patient. Bone and cartilage resection data is generated based at least in part on the prosthesis data, the anatomical data, and the pathoanatomical data. A recommended three-dimensional knee replacement surgeon plan for the patient, comprising the bone and cartilage resection data for facilitating implantation of the prosthesis in the patient, is output.

An individualized kinematic knee replacement analysis computing device includes a memory comprising programmed instructions stored in the memory and one or more processors coupled to the memory that are configured to be capable of executing the programmed instructions stored in the memory to obtain prosthesis data for a selected prosthesis. Anatomical and pathoanatomical data for a specific patient is generated. The anatomical data comprises at least a coronal mechanical lateral distal femoral angle that is specific to the patient. Bone and cartilage resection data is generated based at least in part on the prosthesis data, the anatomical data, and the pathoanatomical data. A recommended three-dimensional knee replacement surgeon plan for the patient, comprising the bone and cartilage resection data for facilitating implantation of the prosthesis in the patient, is output.

A non-transitory computer readable medium having stored thereon instructions for facilitating individualized kinematically aligned knee replacement comprising executable code which when executed by one or more hardware processors, causes the one or more hardware processors to obtain prosthesis data for a selected prosthesis. Anatomical and pathoanatomical data for a specific patient is generated. The anatomical data comprises at least a coronal mechanical lateral distal femoral angle that is specific to the patient. Bone and cartilage resection data is generated based at least in part on the prosthesis data, the anatomical data, and the pathoanatomical data. A recommended three-dimensional knee replacement surgeon plan for the patient, comprising the bone and cartilage resection data for facilitating implantation of the prosthesis in the patient, is output.

This technology has a number of associated advantages including providing methods, non-transitory computer readable media, and individualized kinematic knee replacement analysis computing devices that more effectively and efficiently facilitate individualized kinematically aligned knee replacements resulting in better outcomes for knee replacement patients. In one particular aspect, this technology facilitates performing complex calculations to allow individualized kinematic alignment of a knee replacement. This technology facilitates individualized kinematic alignment by defining bone resections that recreate the kinematic axes of rotation of an individual patient's knee within preferences and limits set by a surgeon, and then computing modifications of bone resections and angles for patients whose anatomy will result in an individualized kinematic plan that exceeds these surgeon preferences and limits.

In one particular example, this technology facilitates correction for a varus limb deformity in a patient who has a coronal mLDFA significantly less than ninety degrees noted on preoperative imaging. Given the patient's individual knee anatomy and pathoanatomy, surgeon preferences and limits are used to compute the coronal angles of the femoral and tibial implants relative to the coronal mechanical axis of the femur and tibia. If ninety degrees minus the measured from the x-ray, MRI or CT scan exceeds the surgeon preferred maximum femoral coronal valgus implant limit, the medial and lateral distal femoral bone resections are adjusted accordingly and the difference of ninety degrees minus the patient's native cornoal mLDFA and the surgeon preferred limit for the maximum femoral coronal valgus angle, is added to the femoral component external rotation angle and the posterior bone resections are adjusted accordingly. If the surgeon elects to make a correction for limb varus that is present pre-operatively, and the limb varus exceeds a threshold value established by the surgeon, the angle of the tibial resection is adjusted by a surgeon-preferred number of degrees. The surgeon sets the maximum tibial implant varus, and if the desired correction will exceed the maximum tibial implant varus, part of the correction may be applied to adjust the tibial implant varus angle, and then part of the correction may be applied to the previously calculated femoral coronal implant angle. This technology performs these complex calculations, generates a relatively precise plan for the surgeon, and efficiently manages the complexity of the surgeon planning process, resulting in a reduced number of errors and improved patient outcomes.

Advantageously, this technology uses two-dimensional or three-dimensional imaging to design a three-dimensional knee replacement plan for each individual patient. With this technology, a surgeon's preferences are used to determine specific actions to be taken based on both an individual patient's anatomy and pathoanatomy. In one example, this technology addresses patient anatomy related to patellofemoral subluxation and tibial tubercle position by facilitating surgeon driven modifications to the bone resections to improve patellofemoral tracking in patients with patellofemoral subluxation or lateral position of tibia tubercle. In another example, this technology addresses patient anatomy related to constitutional varus or valgus by facilitating surgeon-driven modification to the bone resections to allow for residual varus or valgus of the limb in patients who do not have a straight limb preoperatively.

Additionally, the inputs and, subsequently, the surgeon plan generated and output by this technology can advantageously be used by any surgical method to align a knee replacement including CT, MRI, or 2D radiographic-based patient-specific guides, computer navigation including pin and pinless modules, robotic devices, modified conventional instruments, and conventional instruments or other methods used to align a knee replacement.

Accordingly, this technology allows a surgeon to design an individualized kinematic alignment plan, set limits on limb and implant alignment, establish a correction for varus and valgus limbs, as well as reduce patellofemoral subluxation or correct for a laterally placed tibial tubercle. This technology can also track various interrelated bone resections, such as using two-dimensional inputs to produce a three-dimensional plan.

Additionally, this technology can show surgeon planned bone resections, which are used to check proposed bone resections before a bone is cut, as well as compare actual measured bone resections to the planned resections. This technology also reviews surgeon approved suggestions for correction when the resections do not match the plan. The final bone resections can then be recorded in a database for statistical analysis and quality improvement as feedback and input into the process of generating surgeon plans.

Further, this technology advantageously individualizes the knee replacement compared with mechanical alignment. The coronal mLDFA is a coronal angle used to help plan individualized kinematic alignment. With this technology, a surgeon sets preferences and limits in combination with the coronal mLDFA to allow the software to plan the final implant coronal angle of both the femoral and tibial component.

In contrast, when a knee replacement is aligned using a mechanical alignment technique, the mechanical distal femoral angle is not referenced, and any variation in this angle from patient to patient is not considered in the planning process. Accordingly, this technology advantageously takes into account individual variation of the coronal mLDFA and posterior condylar axis and adjusts the bone resections and angles to bring them into compliance with surgeon limits and preferences.

Even further, this technology facilitates database collection of surgeon plans and patient outcomes for continuous improvement of, and feedback for, surgeon plans, as well for comparison purposes with respect to outcomes with mechanically aligned knee replacements. In particular, this technology facilitates collection of preoperative patient demographic data, patient reported outcome scores and range of motion information, along with post operative patient reported outcome scores, satisfaction and reoperation data to allow continuous improvement of the recommended surgeon plan based on outcomes.

Optionally, corresponding data can be obtained for patients with mechanically aligned knee replacements for comparison purposes. Accordingly, specific aspects of executed surgeon plans can advantageously be compared to outcomes, and the results can be used to continually improve the planning process. With this technology, surgeons can review outcomes and determine if changes to the recommended bone resections and/or angles are needed to achieve the best results for an individual patient.

BRIEF DESCRIPTION OF THE DRAWINGS

FIGS. 6A and 6B are tables illustrating an exemplary questionnaire via which surgeon preference data is obtained in one example;

FIG. 7 is a table illustrating an exemplary questionnaire via which observed data for a specific patient is obtained in one example;

FIG. 8 is a table illustrating an exemplary questionnaire via which template data for a specific patient can be obtained in one example;

FIG. 9 is a graphical interface illustrating an exemplary recommended three-dimensional knee replacement surgeon plan for a patient;

DETAILED DESCRIPTION

Figure 1:
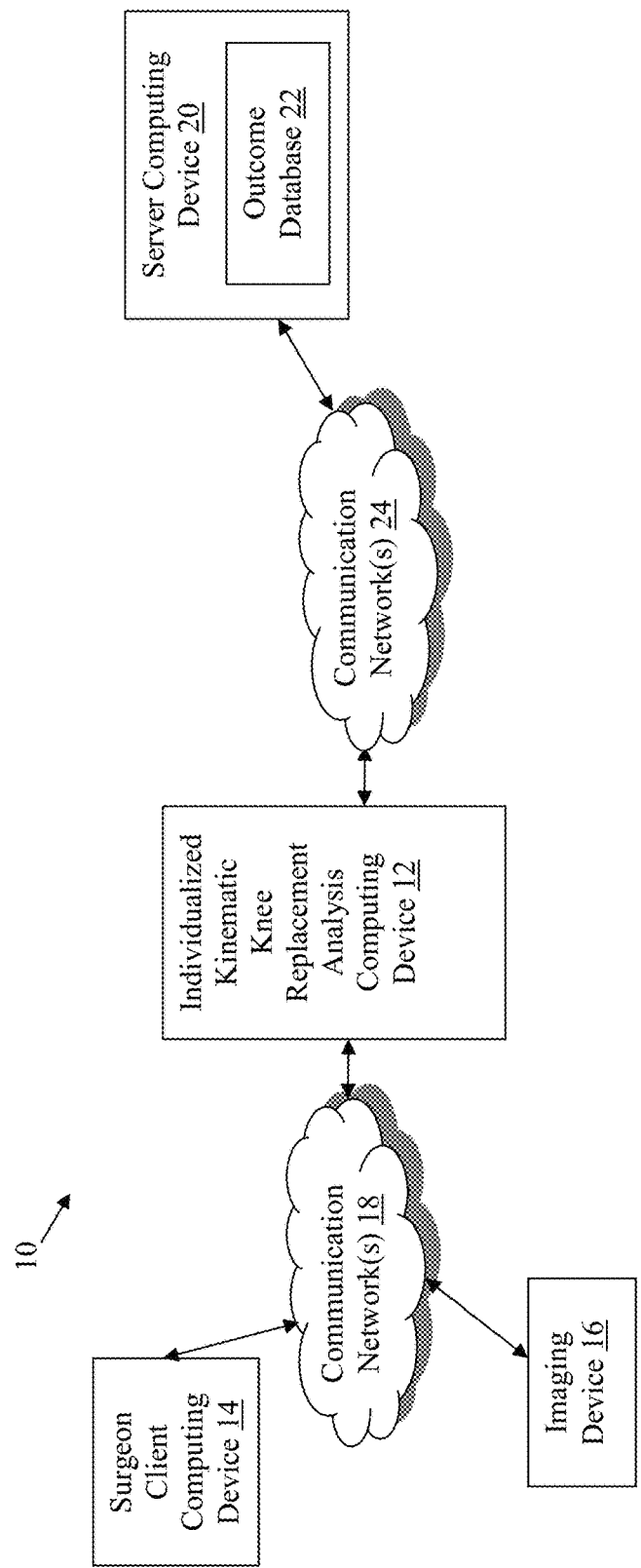
FIG. 1 a block diagram of a network environment with an exemplary kinematic knee replacement (TKR) analysis computing device.

Referring to FIG. 1, a block diagram is shown including an exemplary network environment 10 which incorporates an individualized kinematic knee replacement analysis computing device 12 coupled to a surgeon client computing device 14 and an imaging device 16 via communication network(s) 18 and a server computing device 20 with an outcome database 22 via other communication network(s) 24, although one or more of these devices can be coupled together via other topologies. Additionally, the network environment 10 may include other network devices such as one or more routers and/or switches, by way of example only, which are known to those skilled in the art and will not be described here.

This technology provides a number of advantages including methods, non-transitory computer readable media, and individualized kinematic knee replacement analysis computing devices that efficiently generate a surgeon plan including bone and cartilage resection data that, when used to implant a prosthesis in a patient, results in a relatively effective individualized kinematic alignment for the patient and improved knee replacement outcomes. While this technology is described and illustrated herein with reference to total knee replacements, this technology can also be used in other types of surgeries including, by way of example only, uni-compartmental and bi-compartmental knee replacements.

Figure 2:
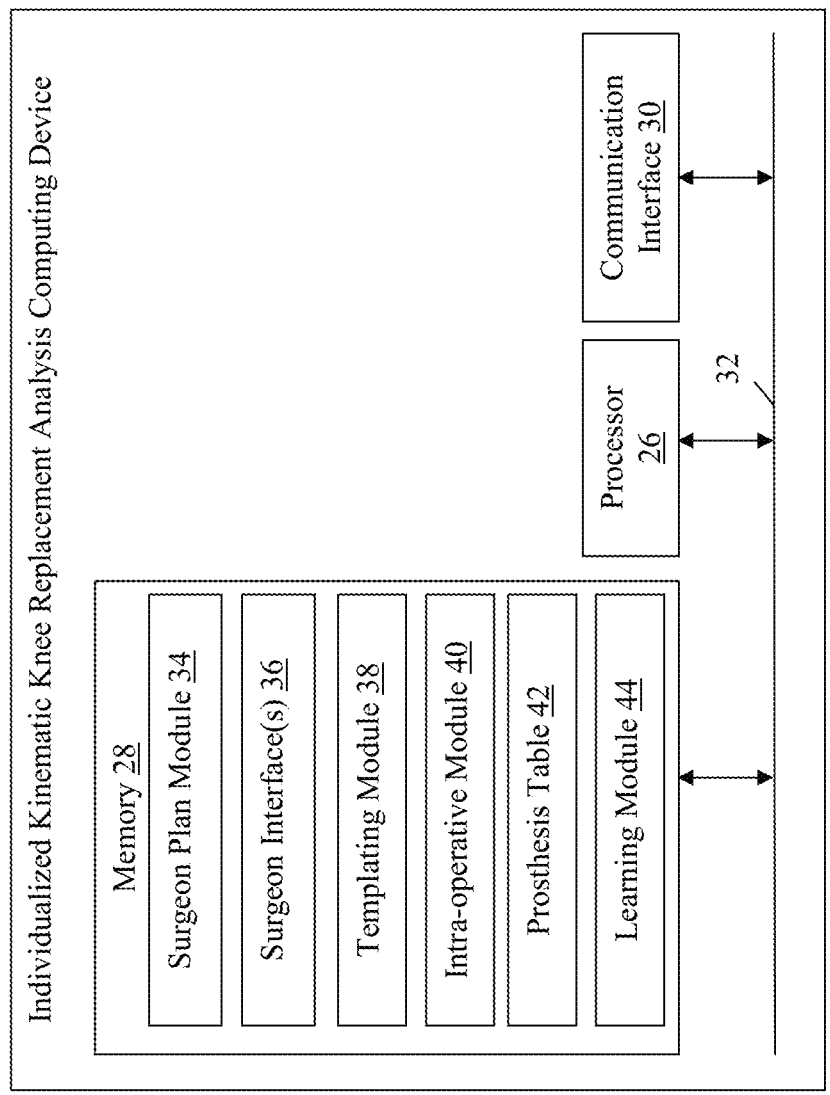
FIG. 2 is a block diagram of the exemplary individualized kinematic knee replacement analysis computing device shown in FIG. 1.

Referring to FIGS. 1-2, the individualized kinematic knee replacement analysis computing device 12 includes a processor 26, a memory 28, and a communication interface 30, which are coupled together by a bus 32 or other communication link, although the individualized kinematic knee replacement analysis computing device 12 may include other types and/or numbers of elements in other configurations. The processor 26 of the individualized kinematic knee replacement analysis computing device 12 may execute programmed instructions stored in the memory 28 of the individualized kinematic knee replacement analysis computing device 12 for the any of the functions described and illustrated herein. The processor 26 of the individualized kinematic knee replacement analysis computing device 12 may include one or more CPUs or general purpose processors with one or more processing cores, by way of example only.

The memory 28 of the individualized kinematic knee replacement analysis computing device 12 stores these programmed instructions for one or more aspects of the present technology, as described and illustrated herein, although some or all of the programmed instructions could be stored or executed elsewhere. A variety of different types of memory storage devices, such as random access memory (RAM), read only memory (ROM), flash, hard disks, solid state drives, or other computer readable media which is read from and written to by a magnetic, optical, or other reading and writing system that is coupled to the processor 26, can be used for the memory 28.

In this particular example, the memory 28 of the individualized kinematic knee replacement analysis computing device 12 includes a surgeon plan module 34, a surgeon interface(s) 36, an optional templating module 38, an optional intra-operative module 40, a prosthesis table 42, and a learning module, although the memory 28 could include other modules, interfaces, tables, or applications in other examples. The surgeon plan module 34 is configured to obtain surgeon preference data, observed data for a patient, template data for the patient, and prosthesis data for a selected prosthesis and to output a recommended three-dimensional knee replacement surgeon plan for the patient, as described and illustrated in more detail later. The recommended three-dimensional knee replacement surgeon plan facilitates implantation of the selected prosthesis in the patient resulting in an individualized kinematic alignment, also as described and illustrated in more detail later.

The surgeon interface(s) 36 in this example include graphical questionnaire interfaces as well as graphical display interface for the recommended three-dimensional knee replacement surgeon plan. The questionnaire interfaces facilitate obtaining the surgeon preference data and observed data for a patient, and optionally the template data for a patient, from a surgeon using the surgeon client computing devices 14, as described and illustrated in more detail later. The graphical display interface is configured to display the recommended three-dimensional knee replacement surgeon plan to a surgeon, thereby conveniently allowing the surgeon to visualize the bone and cartilage resections necessary to implement a knee replacement in an individualized kinematic alignment.

The optional templating module 38 is configured to process radiographic images of a patient, such as images originating with the imaging device 16 for example, to determine template data including anatomical and pathoanatomical data for a patient. The images can be CT, MRI, or x-ray images, for example, although the templating module 38 can be configured to generate template data from other types of radiographic images in other examples.

The optional intra-operative module 40 is configured to obtain measured data subsequent to implementing a three-dimensional knee replacement surgeon plan and to compare the bone and cartilage resection data of the plan and a predetermined kerf with the corresponding measured data. Based on the comparison, the intra-operative module 40 retrieves and outputs recommendations stored by the intra-operative module 40 in the memory 28, as described and illustrated in more detail later.

The prosthesis table 42 stores prosthesis data for a plurality of prosthesis that can be selected for a patient by a surgeon via one of the surgeon interface(s) 36. In one example, the prosthesis data can include a femoral distal medial, distal lateral, posterior medial thickness, posterior lateral prosthesis thickness, tibial prosthesis thickness, or recommended slope, although other information can also be included in the prosthesis data for a selected prosthesis. The prosthesis data is used as an input to generate the bone and cartilage resection data of the recommended three-dimensional knee replacement surgeon plan for a patient, as described and illustrated in more detail later.

The learning module 44 is configured to obtain outcome data correlated with recommended three-dimensional knee replacement surgeon plans for patients, perform a statistical analysis on the correlated data, and update recommended preference data. The updated recommended preference data can then be used as a basis for generating subsequent relatively accurate recommended three-dimensional knee replacement surgeon plans for patients that may lead to improved outcomes, as described and illustrated in more detail later with reference to FIG. 17.

The communication interface 34 of the individualized kinematic knee replacement analysis computing device 12 operatively couples and communicates between the individualized kinematic knee replacement analysis computing device 12 and the surgeon client computing device 14, imaging device 16, and server computing device 20, which are all coupled together by the communication network(s) 18 and 24, although other types and/or numbers of communication networks or systems with other types and/or numbers of connections and configurations to other devices and elements can also be used.

By way of example only, the communication network(s) 18 and 24 can use TCP/IP over Ethernet and industry-standard protocols, although other types and/or numbers of communication networks, can be used. The communication network(s) 18 and 24 in this example may employ any suitable interface mechanisms and network communication technologies including, by way of example only, teletraffic in any suitable form (e.g., voice, modem, and the like), Public Switched Telephone Network (PSTNs), Ethernet-based Packet Data Networks (PDNs), combinations thereof, and the like.

The surgeon client computing device 14 in this example includes a processor, a memory, and a communication interface, which are coupled together by a bus or other communication link, although other types and/or numbers of network devices could be used. The surgeon client computing device 14 may run interface applications, such as Web browsers by way of example only, which may provide an interface to submit information via the surgeon interface(s) 36 to the individualized kinematic knee replacement analysis computing device via the communication network(s) 18. The surgeon client computing device 14 may further include a display device, such as a display screen or touchscreen, and/or an input device, such as a keyboard by way of example only.

In other examples, one or more of the surgeon plan module 34, surgeon interface(s) 36, templating module 38, intra-operative module 40, prosthesis table 42, or learning module 44 are locally deployed and can be located directly on the surgeon client computing device 14. Accordingly, although this technology is described and illustrated herein from the perspective of a remote or web-based deployment of the surgeon plan module 34, surgeon interface(s) 36, templating module 38, intra-operative module 40, prosthesis table 42, and learning module, local and other deployments are also possible and one or more of the surgeon plan module 34, surgeon interface(s) 36, templating module 38, intra-operative module 40, or prosthesis table 42 can also be located elsewhere in the network environment 10.

The imaging device 16 in this example in this example includes a processor, a memory, and a communication interface, which are coupled together by a bus or other communication link, although other types and/or numbers of network devices could be used. The imaging device 16 can be a CT scanning device, an MRI device, or a digital x-ray device, for example, although any other device configured to obtain, store, and/or provide two or three dimensional images of a patient can also be used. The images are used by the templating module 38 to obtain template data in this example, as described and illustrated in more detail earlier.

While the imaging device 16 is illustrated in FIG. 1 as being accessible by the individualized kinematic knee replacement analysis computing device 12 via the communication network(s) 18, accessibility may be limited to the surgeon client computing device 14 or other computing device within a network of a hospital or other medical center, for example. Accordingly, the template data can be obtained by the templating module 38 directly from radiographic images provided by the imaging device 16. Alternatively, the template data can be obtained by the individualized kinematic knee replacement analysis computing device 12 indirectly as provided by templating software hosted by another computing device in the network environment 10 or as input via one of the surgeon interface(s) 36 by a surgeon using the surgeon client computing device 14, for example.

The server computing devices 20 in this example includes a processor, a memory, and a communication interface, which are coupled together by a bus or other communication link, although other types and/or numbers of network devices could be used. Generally, the server computing devices 20 processes requests received from the individualized kinematic knee replacement analysis computing device 12 via the communication network(s) 24 to store and retrieve outcome data stored by the outcome database 22.

The outcome database 22 can be a relational database or any other type of data storage structure configured to store outcome data such as preoperative patient demographic data, patient reported outcome scores, or range of motion information and postoperative patient reported outcome scores, range of motion information, patient satisfaction data, or reoperation data, for example, although other types of outcome data can also be stored in the outcome database 22. Outcome data in this example is stored in the outcome database 22 for knee replacements performed according to this technology and the associated kinematic alignment methods. Optionally, the outcome data can be provided to surgeons to facilitate modification of provided recommended three-dimensional knee replacement surgeon plans, or used to automatically adjust recommended three-dimensional knee replacement surgeon plans for patients in a learning process, as described and illustrated in more detail later. Also optionally, outcome data can be stored in the outcome database 22 for knee replacements performed according to mechanical alignments for comparison purposes.

Although the exemplary network environment 10 with the individualized kinematic knee replacement analysis computing device 14, surgeon client computing device 14, imaging device 16, server computing device 20, and communication network(s) 18 and 24 are described and illustrated herein, other types and/or numbers of systems, devices, components, and elements in other topologies can be used. The systems of the examples described herein are for exemplary purposes, as many variations of the specific hardware and software used to implement the examples are possible, as will be appreciated by those skilled in the relevant art(s).

This technology may also be implemented on computer system(s) that extend across any suitable network using any suitable interface mechanisms and traffic technologies, including by way of example only teletraffic in any suitable form (e.g., voice and modem), wireless traffic media, wireless traffic networks, cellular traffic networks, G3 traffic networks, Public Switched Telephone Network (PSTNs), Packet Data Networks (PDNs), the Internet, intranets, and combinations thereof. Additionally, this technology may be embodied as one or more non-transitory computer readable media having instructions stored thereon for one or more aspects of the technology as described and illustrated by way of the examples herein, which when executed by a processor, cause the processor to carry out the steps necessary to implement the methods of the technology, as described and illustrated herein.

Definitions

The definitions used in this application are for illustrative purposes and do not limit the scope of the invention.

Figure 3:
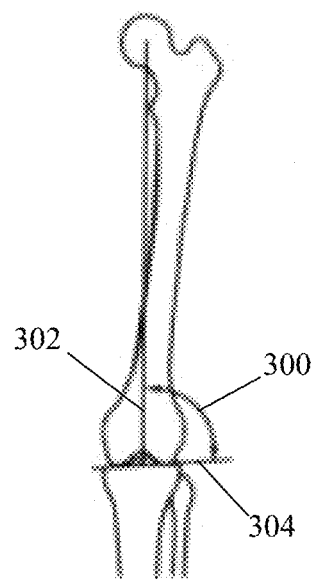
FIG. 3 is a plan view of exemplary femur and tibia bones of an exemplary patient knee.

Referring to FIG. 3, exemplary femur and tibia bones of an exemplary patient knee is illustrated. As used herein, a coronal mechanical lateral distal femoral angle (mLDFA) 300 refers to a lateral angle (e.g., 88.2 degrees) formed from the intersection of the mechanical axis 302 and the knee joint line 304 of the distal femur. The coronal mLDFA can also be expressed in degrees of valgus (or varus) from a 90 degree angle relative to the mechanical axis 302 (e.g., 1.8 degrees valgus), and can then also be referred to as the femoral joint angle.

As used herein, a mechanical axis of the femur refers to a line from a center of a femoral head to a center of an intercondylar notch of a distal femur.

As used herein, a mechanical axis of the tibia refers to a line from a center of a tibial plateau to a center of a talus.

As used herein, an anatomic axis of the femur refers to a line connecting tae center of an intercondylar notch to a point at a center of a femoral shaft 10 cm proximal to a joint line.

As used herein, an anatomic axis of the tibia refers to a line from a center of a tibial plateau to a point at a center of a tibial shaft 10 cm distal to a joint line.

As used herein, a femoral mechanical axis—anatomic axis angle refers to an angle between a femoral mechanical axis and a femoral anatomic axis.

As used herein, a knee joint line of a distal femur refers to a line connecting a most distal aspect of medial and lateral femoral condyles.

As used herein, a hip-knee-ankle angle refers to an angle formed by a mechanical axis of a femur and a tibia.

As used herein, a varus lower limb refers to an inward angulation of a tibia on a coronal limb image, as measured by the hip-knee-ankle angle.

As used herein, a valgus lower limb refers to an outward angulation of a tibia on a coronal limb image, as measured by the hip-knee-ankle angle.

As used herein, a femoral valgus angle relative to an anatomic axis refers to a lateral angle formed from an intersection of an anatomic axis and a knee joint line of a distal femur. The femoral valgus angle relative to an anatomic axis can be expressed in degrees of valgus from a 90 angle to the anatomic axis, for example.

As used herein, a mechanical medial proximal tibial angle refers to an angle between a mechanical axis of a tibia and a tibial plateau, as measured on a medial aspect of the tibia.

As used herein, an angle of the femoral component relative to the mechanical axis refers to an angle between a mechanical axis of a femur and an implant joint line of a distal femur.

As used herein, an angle of a tibial component relative to a mechanical axis refers to an angle between a tibial baseplate and a mechanical axis of a tibia.

As used herein, a femoral distal medial and lateral resection thickness refers to a thickness of bone removed from a femur after distal medial and lateral femoral resections.

As used herein, a femoral external rotation refers to an external rotation of a femur as visualized on axial images, relative to a posterior condylar axis.

As used herein, a femoral posterior medial and lateral resection thickness refers to a thickness of bone removed from a femur after posterior medial and lateral femoral resections.

As used herein, a tibial proximal medial and lateral resection thickness refers to a medial and lateral thickness of bone removed from a tibia after a proximal tibial resection.

As used herein, a tibial resection angle refers to an angle of a tibial resection relative to a mechanical axis of a tibia.

In some examples, one or more of the coronal mLDFA, mechanical axis of the femur, mechanical Axis of the tibia, anatomic axis of the femur, anatomic axis of the tibia, femoral mechanical axis—anatomic axis angle, knee joint line of the distal femur, hip-knee-ankle angle, varus lower limb, valgus lower limb, femoral valgus angle relative to the anatomic axis, mechanical medial proximal tibial angle, angle of the femoral component relative to the mechanical axis, angle of the tibial component relative to the mechanical axis, femoral distal medial and lateral resection thickness, femoral external rotation can be obtained via coronal imaging or other methods, as described and illustrated in more detail later.

As used herein, a sagittal mechanical axis of a tibia refers to a line connecting a center of an ankle to a center of a proximal tibia.

As used herein, a femoral sagittal flexion angle refers to an angle between a line centered in a distal femoral shaft and a line 90 degrees to a femoral implant.

As used herein, a sagittal tibial resection angle (or tibial slope) refers to an angle between a sagittal mechanical axis of a tibia and a lateral tibial plateau.

In some examples, one or more of the sagittal mechanical axis of the tibia, femoral sagittal flexion angle, or sagittal tibial resection angle can be obtained via sagittal imaging or other method, as described and illustrated in more detail later.

Figure 4:
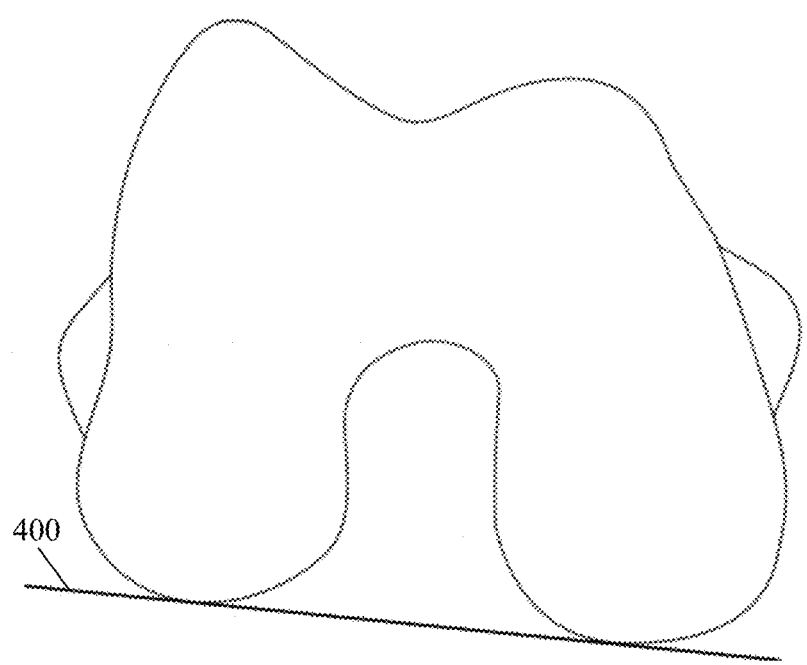
FIG. 4 is a plan view of an exemplary portion of a femur of a patient knee.

Referring to FIG. 4, an exemplary portion of a femur of a patient knee is illustrated. As used herein, a posterior condylar axis 400 refers to a line connecting a most posterior aspect of each of a medial and a lateral femoral condyle.

As used herein, a tibial tubercle position on 3D imaging refers to a position of a medial border of a tibial tubercle in relation to a medial-lateral width of a proximal tibia.

In some examples, one or more of the posterior condylar axis 400 or tibial tubercle position on 3D imaging can be obtained via axial imaging, also as described and illustrated in more detail later.

Figure 5:
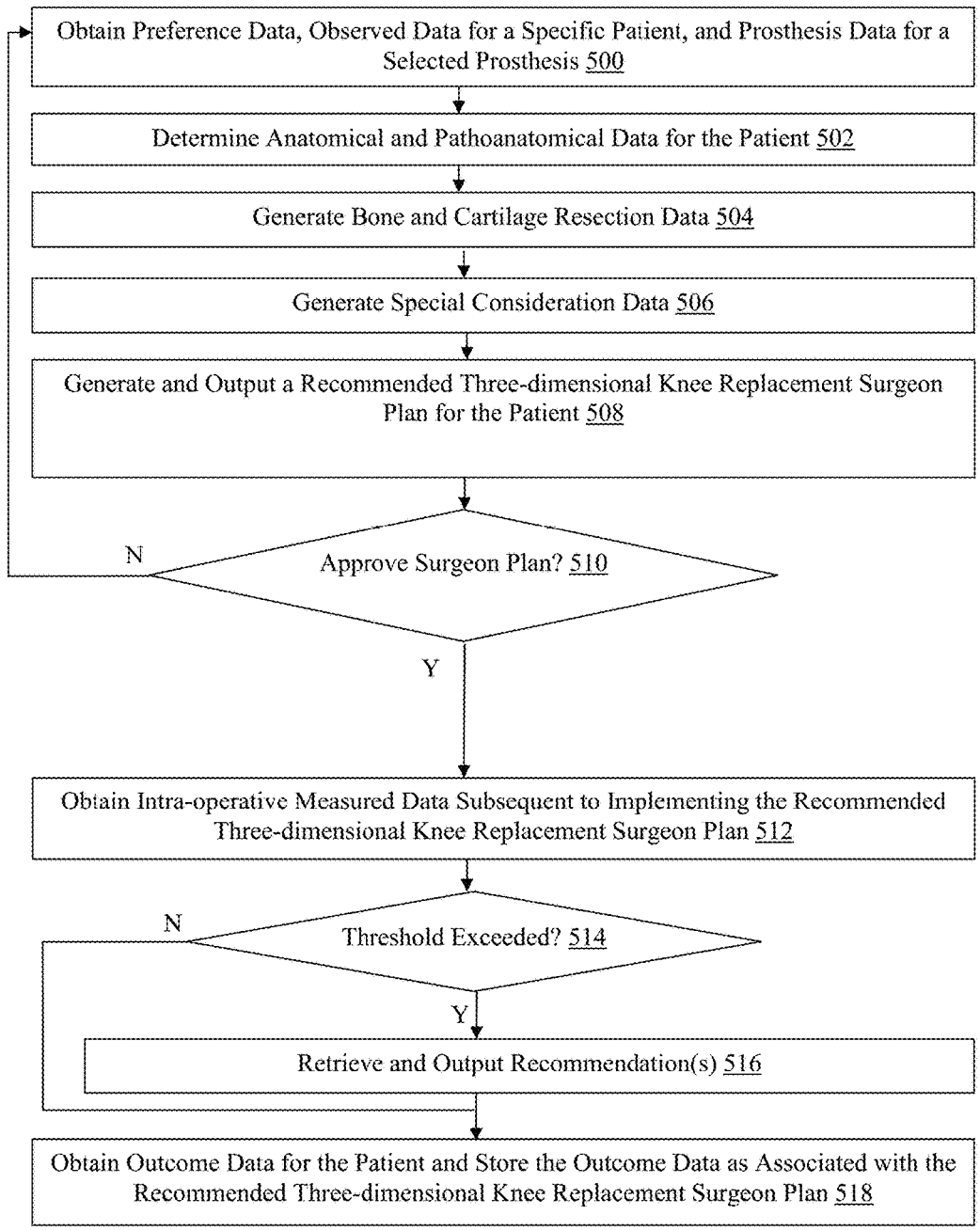
FIG. 5 is a flowchart of an exemplary method for facilitating individualized kinematically aligned knee replacements with the exemplary individualized kinematic knee replacement analysis computing device.

Referring to FIG. 5, an exemplary method for facilitating individualized kinematically aligned knee replacements will now be described. In step 500 in this example, the surgeon plan module 34 of the individualized kinematic knee replacement analysis computing device 12 obtains preference data, observed data for a specific patient, and prosthesis data for a selected prosthesis. The preference data can but submitted via one of the surgeon interface(s) 36 by a surgeon using the surgeon client computing device 14, for example, although other methods of obtaining the preference data can also be used.

Referring to FIGS. 6A and 6B, tables 600 and 602 illustrating an exemplary questionnaire via which surgeon preference data is obtained in one example are shown. The preference data obtained in response to the questions illustrated in tables 600 and 602 can be stored in the memory 28 as corresponding to, for purposes of the examples described and illustrated herein, the variable names illustrated in tables 600 and 602, although other questions and variables names can be used in other examples.

In this example, the questions illustrated in tables 600 and 602 are answered by a surgeon during an initial iteration, and are available for surgeon review and modification as appropriate for each patient. Optionally, standard or default recommendations for each of the questions illustrated in tables 600 and 602 are provided as a reference for the surgeon. In one example, the default recommended preference data is informed by outcome data and modified over time, as described and illustrated in more detail later with reference to FIG. 17. However, the surgeon can use his/her judgment and experience along with patient specific information to input the preference data, and to modify the preference data as needed for each individual patient. In this example, the preference data advantageously limits an alignment of the prosthesis and a limb of the patient to within a predetermined number of degrees of a mechanical axis of a femur, tibia, and limb of the patient, as described and illustrated in more detail later.

In this example, the observed data for a specific patient can also be submitted via one of the surgeon interface(s) 36 by a surgeon using the surgeon client computing device 14, for example, although other methods of obtaining the observed data can also be used. Referring to FIG. 7, a table 700 illustrating an exemplary questionnaire via which observed data for a specific patient is obtained in one example is shown. The observed data obtained in response to the questions illustrated in table 700 can be stored in the memory 28 as corresponding to, for purposes of the examples described and illustrated herein, the variable names illustrated in table 700, although other questions and variables names can be used in other examples. In this example, the questions illustrated in table 700 are answered by a surgeon prior to each iteration for each patient. Optionally, answers to the questions illustrated in table 700 can be restricted to a predetermined set (e.g., "0%, 25%, 50%, 75% or 100%" or "None, Moderate, Severe").

In this example, the individualized kinematic knee replacement analysis computing device 12 receives a selection by a surgeon of a prothesis manufacturer and prosthesis type via the surgeon preference one of the surgeon interface (s) 36. Based on the prosthesis manufacturer and prosthesis type, the individualized kinematic knee replacement analysis computing device 12 obtains prosthesis data from the prosthesis table 42. Accordingly, the prosthesis table 42 can include prosthesis data for a library of knee replacement implants, as described and illustrated in more detail earlier.

Referring back to FIG. 5, in step 502, the individualized kinematic knee replacement analysis computing device 12 determines template data for the patient, optionally from one or radiographic images of the patient, such as coronal, sagittal, patellar/axial, and long leg standing radiographs, for example. In some examples, three-dimensional information from a computerized tomographic scan, magnetic resonance imaging, computer navigation, robotic devices, or other method of providing accurate information for the patient's current anatomy can be used to determine one or more portions of the template data. The template data includes at least anatomical and pathoanatomical data for the patient and the anatomical data includes at least a coronal mLDFA and posterior condylar axis that is specific to the patient.

As described and illustrated in more detail earlier, the template data can be determined by the templating module 38 based on a direct analysis of radiographic images of the patient. In other examples, the template data can be obtained via one of the surgeon interface(s) 36. Referring to FIG. 8, a table 800 illustrating an exemplary questionnaire via which template data for a specific patient can be obtained in one example is shown. The template data obtained in response to the questions illustrated in table 800 can be stored in the memory 28 as corresponding to, for purposes of the examples described and illustrated herein, the variable names illustrated in table 800, although other questions and variables names can be used in other examples. In this example, the questions illustrated in table 800 are answered by a surgeon prior to each iteration for each patient. In yet other examples, other manners of determining the template data can also be used.

In this example, the anatomical data includes, in addition to the coronal mLDFA 300 and posterior condylar axis 400, a coronal femoral mechanical axis of the femur, posterior condylar axis, coronal anatomic axis of the femur, coronal tibial mechanical axis, coronal femoral mechanical axis-anatomic axis angle, sagittal proximal tibial slope, patella thickness, and position of a tibial tubercle of the patient. Additionally, the pathoanatomical data can include a hip knee ankle angle, estimated coronal medial joint line percentage wear, estimated coronal lateral joint line percentage wear, estimated coronal medial femoral condyle wear, estimated coronal lateral femoral condyle wear, estimated patellofemoral subluxation, and sagittal patellar thickness adjusted from a sagittal magnification adjusted radiograph. However, other anatomical and/or pathoanatomical data can also be used in other examples. Optionally, additional magnification corrected size measurements can be stored and compared with a table of prosthesis sizes stored in the memory 28 to facilitate selection of the correct size prosthesis, and to adjust femoral sagittal flexion as needed.

Referring back to FIG. 5, in step 504, the surgeon plan module 34 of the individualized kinematic knee replacement analysis computing device 12 generates bone and cartilage resection data based on the preference data, observed data for the patient, prosthesis data for the selected prosthesis, anatomical data, and pathoanatomical data. In this example, the bone and cartilage resection data includes a femoral component coronal alignment angle relative to a coronal mechanical axis of a femur of the patient, femoral component coronal alignment angle relative to a coronal anatomic axis of the femur, femoral distal medial resection thickness, femoral distal lateral resection thickness, femoral component axial external rotation angle, femoral posterior medial resection thickness, femoral posterior lateral resection thickness, tibial component coronal alignment angle relative to the coronal mechanical axis of a tibia of the patient, tibia medial resection thickness, tibia lateral resection thickness, and tibia sagittal slope. The bone and cartilage resection data can be generated as described and illustrated in more detail later with reference to FIGS. 10-18.

In step 506, the surgeon plan module 34 of the individualized kinematic knee replacement analysis computing device 12 optionally determines whether one or more special considerations are applicable based on one or more of the preference data, the observed data, the prosthesis data, or the anatomical and/or pathoanatomical data and generates corresponding special consideration data, also as described and illustrated in more detail later with reference to FIGS. 10-18.

In one example, the special considerations include whether there is a need for one or more releases, an additional external rotation of a femoral component, or a relatively narrow component in a same family as the selected prosthesis, although other special considerations can also be used in other examples.

In step 508, the surgeon plan module 34 of the individualized kinematic knee replacement analysis computing device 12 generates and outputs a recommended three-dimensional knee replacement surgeon plan for the patient. The recommended three-dimensional knee replacement surgeon plan for the patient includes at least the bone and cartilage resection data generated in step 504 and optionally includes the special consideration data and/or an indication of one or more portions of the preference data, observed data for the patient, or prosthesis data for the selected prosthesis (e.g., whether the surgeon has selected a posterior stabilized implant).

Referring to FIG. 9, a graphical interface 900 illustrating an exemplary recommended three-dimensional knee replacement surgeon plan for a patient is shown. In this example, the graphical interface include distal femur, posterior femur, and tibia bone and cartilage resection data, as well as special consideration data of recommended three-dimensional knee replacement surgeon plan generated in step 508 and optionally modified in step 512. In other examples, other manners of outputting the recommended three-dimensional knee replacement surgeon plan can also be used.

Referring back to FIG. 5, in step 510, the surgeon plan module 34 of the individualized kinematic knee replacement analysis computing device 12 determines when the surgeon has approved the recommended three-dimensional knee replacement surgeon plan for the patient. Accordingly, the graphical display output to the surgeon client computing device 14 can include a button or other feature facilitating an input indicating approval from a surgeon user of the surgeon client computing device 14, although other methods of determining whether the output recommended three-dimensional knee replacement surgeon plan for the patient is approved by the surgeon can also be used.

If the individualized kinematic knee replacement analysis computing device 12 determines that the surgeon has not approved the recommended three-dimensional knee replacement surgeon plan for the patient, then the No branch is taken back to step 500 and one or more revised portions of the preference data, observed data, or prosthesis data are obtained, and steps 502-510 are repeated based on the revised input(s). However, if the individualized kinematic knee replacement analysis computing device 12 determines that the surgeon has approved the recommended three-dimensional knee replacement surgeon plan for the patient, then the Yes branch is taken to step 512.

Accordingly, the output recommended three-dimensional knee replacement surgeon plan includes at least the bone and cartilage resection data for facilitating implantation of the selected prosthesis in the patient in an individualized kinematic alignment. Generally, in order to implement the recommended three-dimensional knee replacement surgeon plan in some examples, a surgeon can cut a femur of the patient optionally using a femoral guide (also referred to as a jig) set based at least in part on the femoral valgus angle relative to anatomic axis and the external rotation of the femur of the recommended three-dimensional knee replacement surgeon plan. Additionally, the surgeon can cut a tibia of the patient optionally using a tibial guide set based at least in part on the tibial varus angle, the medial tibial cut thickness, and the lateral tibial cut thickness of the recommended three-dimensional knee replacement surgeon plan.

Optionally, a manufacturer of the selected prosthesis or other third party, for example, can form one or more femoral and/or one or more tibial guides specific to the patient based on the three-dimensional knee replacement surgeon plan output in step 508. The guides can be formed using three-dimensional printing, for example, although any other method of forming the guides can also be used. Accordingly, in this example, the femoral and tibial guides are advantageously configured to facilitate cutting of a femur and a tibia of the patient, respectively, to facilitate individualized kinematic alignment of a limb of the patient upon implantation of the prosthesis. Accordingly, many different methods can be used to accurately align a knee replacement at surgery using the recommended three-dimensional knee replacement surgeon plan output in step 508 in order to pre-plan a surgery and execute the surgical procedure, some examples of which will now be described, although many other types of methods can also be used in other examples.

Conventional Instruments

In this example, a surgeon can use the recommended three-dimensional knee replacement surgeon plan to plan a surgery for a patient that is carried out using standard or modified conventional instruments. In particular, a long alignment rod is placed from the distal femur into the intramedullary canal. A guide for the distal femoral valgus resection angle is then set based on the femoral valgus angle relative to anatomic axis of the recommended three-dimensional knee replacement surgeon plan.

A distal femoral cutting guide is then pinned in place, checked to verify proposed resection thicknesses, adjusted as needed, and then the distal medial and distal lateral femoral resections are made with a surgical saw using the distal femoral cutting guide. A surgical saw is placed through the slot or the surface of the guide, and the bone resections at the distal medial and distal lateral femoral condyles are made by sawing the bone from anterior to posterior. When the saw cut is complete, the resected piece of bone and cartilage is removed from the patient and measured with surgical measuring calipers to determine the thickness of the resected bone and cartilage.

Because the saw blade causes a small amount of bone to be turned into fine particles, similar to a wood blade creating sawdust, the thickness of this bone is determined as related to the thickness of the sawblade, which is called kerf. The surgeon selects a preference for the thickness of the kerf based on the particular sawblade used, and adds this back to the thickness of the bone and cartilage measured by the calipers to determine a final thickness measurement of the resected bone and cartilage. This result can then be compared to the distal medial and distal lateral resection thicknesses of the recommended three-dimensional knee replacement surgeon plan. The surgeon then accepts the bone cut or makes a correction to more precisely attain the surgeon plan resection thickness.

The external rotation of the femur of the recommended three-dimensional knee replacement surgeon plan can then be used to set the external rotation using a conventional external rotation alignment guide set to the appropriate size femoral component. An anterior posterior chamfer cut guide is placed in the holes made according to the desired external rotation and the proposed cuts are viewed, and the guide adjusted as needed. The bone cuts are then made through the slot or aligned with the metal surface of the cutting guide, and the thickness of the bone and cartilage is measured for the posterior medial and posterior lateral resected pieces of bone. Adding a correction for the kerf of the saw blade produces a final thickness measurement that can then be compared to the number of millimeters on the surgeon plan for the posterior medial and posterior lateral resection thicknesses. The surgeon then accepts the bone cut or makes a correction to more precisely attain the resection thickness indicated in the recommended three-dimensional knee replacement surgeon plan.

The tibial resections can then be made according to the tibial varus angle of the recommended three-dimensional knee replacement surgeon plan, and the medial and lateral tibial resection thicknesses. Initially, an external tibial alignment guide is set into varus at roughly the desired amount according to the surgeon plan. A stylus placed through the tibial cutting slot can then be used to more precisely guide the exact thickness of medial and lateral resections and the external alignment guide varus is adjusted to achieve these resections. The bone cuts are then made through the slot or aligned with the metal surface of the cutting guide, and the thickness of the bone and cartilage is measured for the medial and lateral tibial thickness. Adding a correction for the kerf of the saw blade produces a final thickness measurement that is then compared to the number of millimeters on the surgeon plan for the tibial medial and lateral resection thicknesses. The surgeon then accepts the bone cut or makes a correction to more precisely attain the resection thickness indicated in the recommended three-dimensional knee replacement surgeon plan.

Alternatively the surgeon can elect to gap balance the tibia off the previously resected surface of the femur. Initially, the external tibial alignment guide is set into varus at roughly the desired amount according to the recommended three-dimensional knee replacement surgeon plan. The surgeon visually balances the gap between the tibia and femur, and makes an initial cut at the thickness indicated in the recommended three-dimensional knee replacement surgeon plan using the stylus as a guide. Spacer blocks are placed in flexion and extension, ligament tension is assessed manually, and a correction of any imbalance is achieved by a second compensatory cut.

Once all of the femoral and tibial bone resections are performed in accordance with the recommended three-dimensional knee replacement surgeon plan, the tibia, femur and patella are prepared and cleansed. The correct size tibia, femur and patella implants are inserted with or without cement to the bone to compete the implantation process for the knee replacement.

Patient-Specific Guides

In another example, the recommended three-dimensional knee replacement surgeon plan can be used in conjunction with a manufacturer's computer planning tool and patient specific guide(s), planning the bone cuts and resection angles to achieve the surgeon preferred, individualized kinematic plan. In this example, the recommended three-dimensional knee replacement surgeon plan can be exported to the manufacturer's planning tool to determine the final plan and sizing of the implant, which can be presented to the surgeon. Specifically, the surgeon reviews the manufacturer computer plan and modifies or approves the plan prior to fabrication of the patient specific guide. The guide is then manufactured to accurately fit the exact anatomy of a particular patient, and is precisely fabricated to allow accurate cutting of the bone to achieve the surgeon preferred, individualized kinematic plan. At the time of surgery, the sterile guides are opened on the surgical field, and identified through patient specific identifiers as belonging to the correct patient.

Once the surgeon exposes the knee anatomy, a femoral one of the patient specific guides is placed onto the femur at the knee, in a specific position and precisely fit to the patient's specific anatomy. The patient specific femoral guide is pinned in place and drill holes for the rotation and proper size of the prosthesis are made in the distal articular surface of the patient's femur. The proposed anterior to posterior resections at the distal medial and/or distal lateral femur are checked to verify satisfactory fabrication of the guide to the surgeon preferred specifications, as noted on the recommended three-dimensional knee replacement surgeon plan.

The bone resections are then made through the slot in the patient specific femoral guide, or through a separate metal cutting guide placed over the retained pins in the anterior distal femur after removing the patient specific femoral guide. A surgical saw is placed through the slot, and the bone resections at the distal medial and distal lateral femoral condyles are made by sawing the bone from anterior to posterior. When the saw cut is complete, the resected piece of bone and cartilage is removed from the patient and measured with a surgical measuring caliper to determine the thickness of the resected bone and cartilage.

Optionally, as described and illustrated earlier, the surgeon can select a preference for the thickness of the kerf based on the particular saw blade used, and add this back to the thickness of the bone and cartilage measured by the calipers to determine a final thickness measurement of the resected bone and cartilage. This result is then compared to the distal medial and distal lateral resection thicknesses of the recommended three-dimensional knee replacement surgeon plan. The surgeon then accepts the bone cut or makes a correction to more precisely attain the surgeon plan resection thickness.

After making the distal femoral resections, the surgeon removes the pins and cutting guide from the distal femur, and places a size specific manufacturer's anterior posterior chamfer cutting guide into the holes previously drilled in the articular surface of the distal femur. The proposed resections are checked to verify they match the surgeon preferred posterior resections and that the anterior resection is satisfactorily aligned with the anterior distal femoral cortex. The bone cuts are then made through the slot or aligned with the metal surface of the patient specific femoral guide, and the thickness of the bone and cartilage is measured for the posterior medial and/or posterior lateral resected pieces of bone. Adding a correction for the kerf of the saw blade produces a final thickness measurement that is then compared to the posterior medial and posterior lateral resection thicknesses of the recommended three-dimensional knee replacement surgeon plan. The surgeon then accepts the bone cut or makes a correction to more precisely attain the surgeon plan resection thickness.

After preparing the proximal tibia to accept a tibial one of the patient specific guides, the guide is fit to the bone, pinned in place and checked by one of several methods to ascertain accurate placement and alignment in the coronal and sagittal plane for the proposed bone resections. Either through the slot in the patient specific tibial guide or through a metal guide placed over the retained pins after the patient specific tibial guide is removed, the bone resection at the proximal tibial surface is created with the surgical saw. The thickness of the medial and lateral resected bone is measured with the calipers, a correction for the kerf is added, and the medial and/or lateral tibial resection thicknesses are compared with the recommended three-dimensional knee replacement surgeon plan. The surgeon then accepts the bone cuts or makes a correction to more precisely attain the surgeon plan resection thicknesses.

Once all of the femoral and tibial bone resections are performed in accordance with the recommended three-dimensional knee replacement surgeon plan, the tibia, femur and patella if desired, are prepared and cleansed. The correct size tibia, femur and patella implants are inserted with or without cement to the bone to compete the implantation process for the knee replacement.

Computer Navigation System

In yet another example, the recommended three-dimensional knee replacement surgeon plan can be utilized in the context of a computer navigation system. In this example, a computer navigation device can calculate a center of rotation of a femur, detect a knee articular surface anatomy and boundaries, and ankle boundaries, which can be used to provide the anatomic and pathoanatomic inputs, including mLDFA, posterior condylar axis, and tibial slope.

Alternatively, the resection angles and resections thickness of the recommended three-dimensional knee replacement surgeon plan can be used directly by a computer navigation system, such as an accelerometer based system, to allow placement of pins and intra-operative metal or plastic cutting guide to allow resection of the distal medial and lateral femur, posterior medial and posterior lateral femur and proximal medial and/or lateral tibia to the desired angles and thicknesses as detailed in the recommended three-dimensional knee replacement surgeon plan. Intra-operatively, the computer navigation system can guide the surgeon to the correct bone resections and angles needed to achieve surgeon driven individualized kinematic plan within the limits set by the surgeon.

The computer navigation system can be used to place a distal femoral cutting guide. The proposed anterior to posterior resections at the distal medial and/or distal lateral femur are checked to verify satisfactory resection to the surgeon preferred specifications. The bone resections are then made through a cutting guide placed over the pins in the anterior distal femur. A surgical saw is placed through the slot, and the bone resections at the distal medial and distal lateral femoral condyles are made by sawing the bone from anterior to posterior. When the saw cut is complete, the resected piece of bone and cartilage is removed from the patient and measured with surgical measuring calipers to determine the thickness of the resected bone and cartilage.

Optionally, as described and illustrated earlier, the surgeon can select a preference for the thickness of the kerf based on the particular saw blade used, and add this back to the thickness of the bone and cartilage measured by the calipers to determine a final thickness measurement of the resected bone and cartilage. This result is then compared to the distal medial and/or distal lateral resection thicknesses of the recommended three-dimensional knee replacement surgeon plan. The surgeon then accepts the bone cut or makes a correction to more precisely attain the surgeon plan resection thickness.

The external rotation of the femur of the recommended three-dimensional knee replacement surgeon plan is used to set the external rotation using the computer navigation, adjusted to the proper femoral implant size and set to the external rotation of the recommended three-dimensional knee replacement surgeon plan. The anterior posterior chamfer cut guide is placed in the holes made according to the desired external rotation and the proposed cuts are viewed, and the guide adjusted as needed. The bone cuts are then made through the slot or aligned with the metal surface of the cutting guide, and the thickness of the bone and cartilage is measured for the posterior medial and/or posterior lateral resected pieces of bone. Adding a correction for the kerf of the saw blade produces a final thickness measurement that is then compared to the posterior medial and/or posterior lateral resection thicknesses of the recommended three-dimensional knee replacement surgeon plan. The surgeon then accepts the bone cut or makes a correction to more precisely attain the resection thickness of the recommended three-dimensional knee replacement surgeon plan.

The tibial resections can then be made according to the tibial varus angle and slope and the medial and lateral tibial resection thicknesses of the recommended three-dimensional knee replacement surgeon plan. The computer navigation system allows visual feedback to the surgeon of the varus angle, slope and depth of resection to allow pinning of the tibial cutting block to the proximal femur according to the recommended three-dimensional knee replacement surgeon plan. A stylus placed through the tibial cutting slot can then be used to check the thickness of medial and lateral resections. The bone cuts are then made through the slot or aligned with the metal surface of the cutting guide, and the thickness of the bone and cartilage is measured for the medial and lateral tibial thickness. Adding a correction for the kerf of the saw blade produces a final thickness measurement that is then compared to the tibial medial and/or lateral resection thicknesses of the recommended three-dimensional knee replacement surgeon plan. The surgeon then accepts the bone cut or makes a correction to more precisely attain the surgeon plan resection thickness.

Once all of the femoral and tibial bone resections are performed in accordance with the recommended three-dimensional knee replacement surgeon plan, the tibia, femur and patella are prepared and cleansed. The correct size tibia, femur and patella implants are inserted with or without cement to the bone to compete the implantation process for the knee replacement.

Robotic-Assisted Surgery

In another example, a computer navigation system that uses a robotic arm set to limit the extent of resections at the femur and tibia, while allowing the proper depth of resection and angle for each bone resection in the surgeon plan can be used, for example using a haptic system. The recommended three-dimensional knee replacement surgeon plan can be loaded into the robotic arm system, which is then used to create the bone resections by burr, saw or other method to allow placement of the tibial and femoral components in the precise location detailed by the recommended three-dimensional knee replacement surgeon plan.

Once all of the femoral and tibial bone resections are performed in accordance with the recommended three-dimensional knee replacement surgeon plan, the tibia, femur and patella are prepared and cleansed. The correct size tibia, femur and patella implants are inserted with or without cement to the bone to compete the implantation process for the knee replacement.

Referring back to FIG. 5, in step 512, the intra-operative module 40 of the individualized kinematic knee replacement analysis computing device 12 obtains measured data subsequent to implementing the recommended three-dimensional knee replacement surgeon plan for the patient, as described and illustrated earlier by way of the examples. The measured data corresponds with the various bone and cartilage resections performed according to the bone and cartilage resection data of the three-dimensional knee replacement surgeon plan.

Accordingly, in one example, the surgeon can measure the distal medial femoral resection thickness, the distal lateral femoral resection thickness, the posterior medial femoral resection thickness, and the posterior lateral femoral resection thickness, the minimal medial tibial resection, the minimal lateral tibial resection, and the residual patellar thickness, although other numbers and types of measured data can also be obtained. The measured data can be initially obtained by a surgeon and input to the individualized kinematic knee replacement analysis computing device 12 via one of the surgeon interface(s) 36 provided to the surgeon client computing device 14, for example, although other manners of obtaining the measured data can also be used.

In step 514, the intra-operative module 40 individualized kinematic knee replacement analysis computing device 12 determines whether a threshold is exceeded for any portion of the measured data. The bone and cartilage resection data represents the desired values for the various resections and the measured data represents the actual values for the resections subsequent to implementing the three-dimensional knee replacement surgeon plan and cutting the femur and tibia of the patient. Accordingly, the threshold can be exceeded when a portion of the measured data and a predetermined kerf deviates from a corresponding portion of the bone and cartilage resection data by a predetermined amount or percentage, for example. If the individualized kinematic knee replacement analysis computing device 12 determines a threshold is exceeded for at least one portion of the measured data, then the Yes branch is taken to step 516.

In step 516, the intra-operative module 40 individualized kinematic knee replacement analysis computing device 12 retrieves from the memory 28 and outputs one or more recommendations for managing the deviation in the measured data. In one example, the intra-operative module 40 individualized kinematic knee replacement analysis computing device 12 indicates recommendations if the resections are 1 mm or more less than the desired femoral resection, 2 mm or more less than the desired tibial resections, and 2 mm or more thicker than the desired residual patellar thickness, based on the surgeons preferences, although other preferences and threshold values can also be used in other examples. The recommendation(s) can be retrieved based on the portion of the measured data for which the corresponding threshold was exceeded, for example, although the recommendation(s) can also be retrieved based on other factors in other examples.

Subsequent to retrieving and outputting the recommendation(s), or if the individualized kinematic knee replacement analysis computing device 12 determines in step 514 that a threshold is not exceeded for any portion of the measured data and the No branch is taken, the individualized kinematic knee replacement analysis computing device 12 proceeds to step 518. In step 518, the individualized kinematic knee replacement analysis computing device 12 obtains outcome data for the patient and sends the outcome data to the server computing device 20 to be stored in the outcome database as associated with the bone and cartilage resection data, and optionally other information, such as other portion(s) of the recommended three-dimensional knee replacement surgeon plan and/or demographic information corresponding to the patient, for example.

Figure 19:
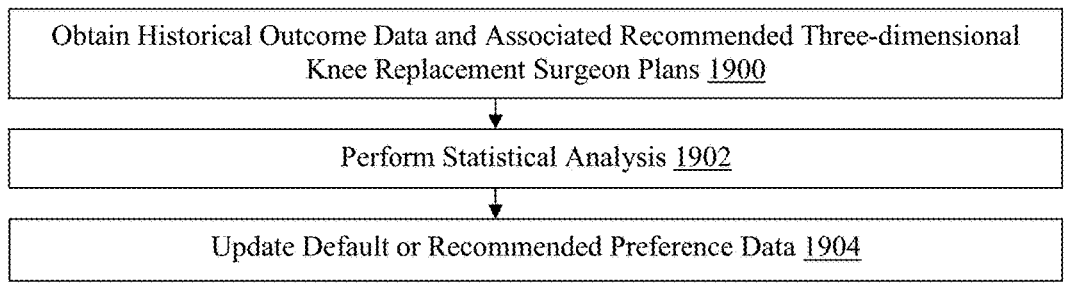
FIG. 19 is a flowchart of an exemplary method for updating default recommended preference data based on historical outcome data.

In one example, six months, one year, and annually thereafter subsequent to performing the knee replacement surgery, the individualized kinematic knee replacement analysis computing device 12 can automatically send an outcome questionnaire to each patient using stored contact information, and store information submitted by the patient via the outcome questionnaire. The information can include range of motion data, one or more outcome scores, patient satisfaction data, and/or reoperation data, for example, although other outcome information can also be obtained and/or stored in the outcome database 22. The outcome database 22 can be used by the individualized kinematic knee replacement analysis computing device 12 as described and illustrated in more detail later with reference to FIG. 19, for example.

Figure 10:
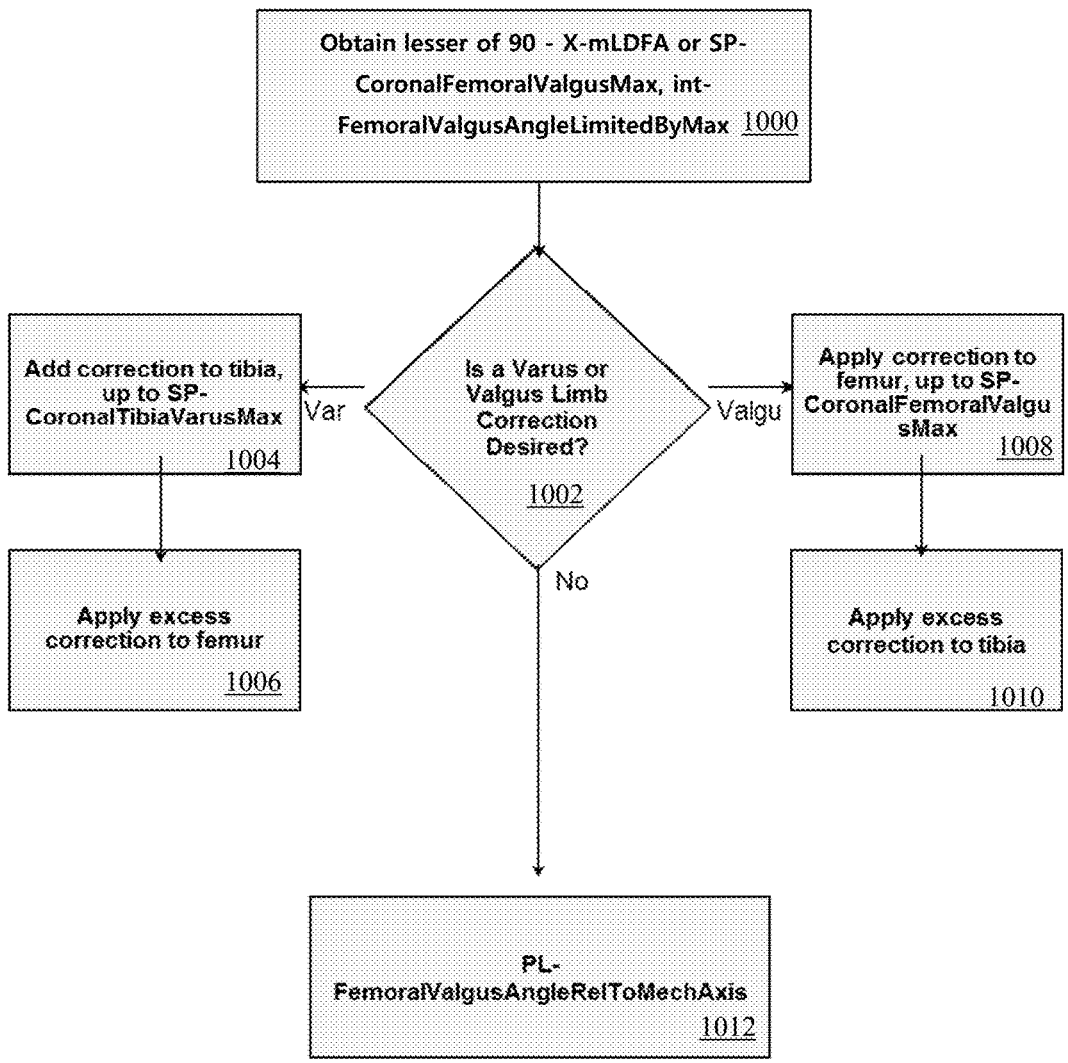
FIG. 10 is a flowchart of an exemplary method for generating a femoral valgus angle relative to a mechanical axis for a specific patient.

Exemplary methods for generating the bone and cartilage resection data in step 504 will now be described in more detail with reference to FIGS. 10-18. Referring to FIG. 10, an exemplary method for generating a femoral valgus angle relative to a mechanical axis (PL-FemoralValgusAngleRelToMechAxis) for a specific patient will now be described. In step 1000 in this example, the Individualized kinematic knee replacement analysis computing device 12 determines an intermediate femoral resection angle (int-FemoralValgusAngleLimitedByMax) based on the lesser of 90 minus the coronal mLDFA (X-mLDFA) or the surgeon preference maximum femoral implant valgus (SP-CoronalFemoralValgusMax).

In this example, the intermediate femoral resection angle is modified for a varus or valgus limb correction. Accordingly, in step 1002, the individualized kinematic knee replacement analysis computing device 12 determines, based on a varus limb correction (SP-LimbVarusCorrectionAmount) and a valgus limb correction (SP-LimbValgusCoronalCorrectionAmount), whether a varus or valgus limb correction is desired. If the individualized kinematic knee replacement analysis computing device 12 determines that a varus limb correction is desired, then the varus branch is taken to step 1004. In step 1004, the individualized kinematic knee replacement analysis computing device 12 applies the varus limb correction (SP-Limb VarusCorrectionAmount) to the tibia by increasing the tibial varus angle up to a maximum tibial varus angle (SP-CoronalTibiaVarusMax).

However, if the full correction cannot be made because a maximum tibial varus value (SP-CoronalTibiaVarusMax) is reached, then an excess correction (int-ExcessVarusLimbCorrection) is determined and applied to the femur, in step 1006, by subtracting the excess correction (int-ExcessVarusLimbCorrection) from the femoral resection angle (int-FemoralValgusAngleLimitedByMax), thereby resulting in the femoral valgus angle relative to a mechanical axis (PL-FemoralValgusAngleRelToMechAxis).

Referring back to step 1002, if the individualized kinematic knee replacement analysis computing device 12 determines that a valgus limb correction is desired, then the valgus branch is taken to step 1008. In step 1008, the individualized kinematic knee replacement analysis computing device 12 applies the limb correction to the femur by adding the valgus correction amount (SP-Limb ValgusCoronalCorrectionAmount) to the coronal mLDFA (X-mLDFA) up to the maximum implant valgus angle (SP-CoronalFemoralValgusMax), thereby resulting in the femoral valgus angle relative to a mechanical axis (PL-FemoralValgusAngleRelToMechAxis). In step 1010, the individualized kinematic knee replacement analysis computing device 12 applies any excess correction to the tibia by decreasing the tibial varus angle.

Referring again to step 1002, if the individualized kinematic knee replacement analysis computing device 12 determines that varus or valgus limb correction is not desired then the No branch is taken to step 1012. In step 1012 the individualized kinematic knee replacement analysis computing device 12 sets the femoral valgus angle relative to a mechanical axis (PL-FemoralValgusAngleRelToMechAxis) equal to the result of step 1000.

Figure 11:
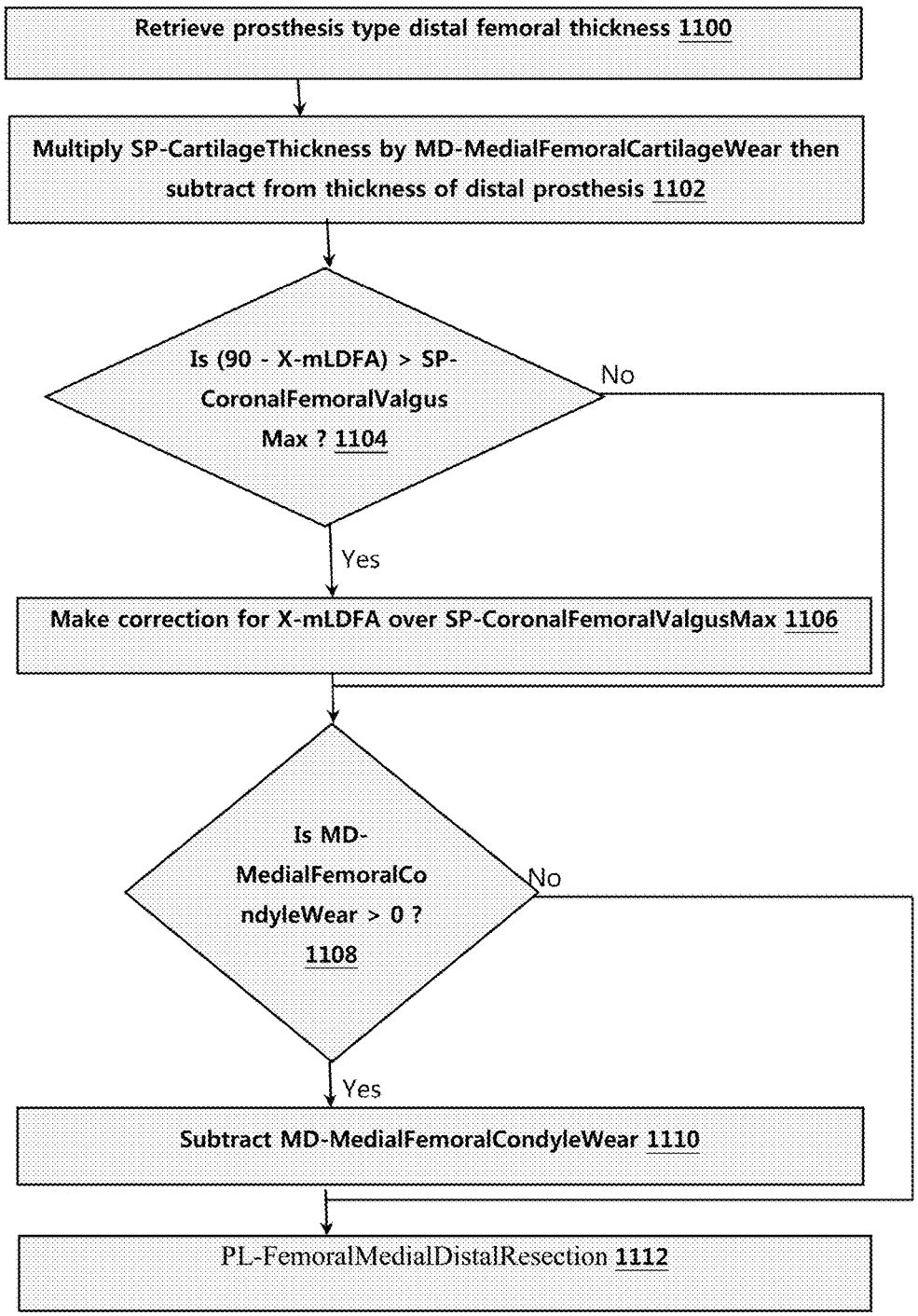
FIG. 11 is a flowchart of an exemplary method for generating a femoral distal medial resection thickness for a specific patient.

Referring to FIG. 11, an exemplary method for generating a femoral distal medial resection thickness (PL-FemoralMedialDistalResection) for a specific patient will now be described. In step 1100 in this example, the individualized kinematic knee replacement analysis computing device 12 retrieves a prosthesis type distal femoral thickness from the prosthesis table 42. In step 1102, the individualized kinematic knee replacement analysis computing device 12 multiplies a default thickness of medial cartilage (SP-CartilageThickness) by a percentage of medial wear (MD-MedialFemoralCartilageWear), and then subtracts the result from the thickness of the distal prosthesis obtained in step 1100.

Next, the individualized kinematic knee replacement analysis computing device 12 determines whether to accept the manufacturer's thickness of the prosthesis for femoral resection planning based on the surgeon preference data (SP-AdjustManufacturerDistalFemoralThickness). If the individualized kinematic knee replacement analysis computing device 12 determines that the manufacturer's thickness of the prosthesis should be accepted, then the distal medial resection thickness (PL-FemoralMedialDistalResection) is not changed. However, if the individualized kinematic knee replacement analysis computing device 12 determines that the manufacturer's thickness of the prosthesis should not be accepted, then the distal medial resection thickness (PL-FemoralMedialDistalResection) is modified by adding an amount determined based on the surgeon preference data (SP-DistalFemoralThicknessAdjustment).

In step 1104, the individualized kinematic knee replacement analysis computing device 12 determines whether 90 minus the coronal mLDFA (X-mLDFA) exceeds a threshold determined based on the surgeon preference data (SP-CoronalFemoralValgusMax). If the individualized kinematic knee replacement analysis computing device 12 determines that 90 minus the coronal mLDFA (X-mLDFA) exceeds the threshold, then the Yes branch is taken to step 1106. In step 1106, the individualized kinematic knee replacement analysis computing device 12 modifies the distal medial resection thickness (PL-FemoralMedialDistalResection) by increasing the distal medial resection thickness (PL-FemoralMedialDistalResection) by the difference of the actual lateral thickness and the corrected lateral thickness for less valgus than anatomically present.

Subsequent to making the correction in step 1106, or if the individualized kinematic knee replacement analysis computing device 12 determines in step 1104 that 90 minus the coronal mLDFA (X-mLDFA) does not exceed the threshold and the No branch is taken, the individualized kinematic knee replacement analysis computing device 12 proceeds to step 1108. In step 1108 the individualized kinematic knee replacement analysis computing device 12 determines whether there is medial femoral condyle bone wear on the coronal view based on the observed data (MD-MedialFemoralCondyleWear). If the individualized kinematic knee replacement analysis computing device 12 determines that there is medial femoral condyle bone wear on the coronal view, then the Yes branch is taken to step 1110.

In step 1110, the individualized kinematic knee replacement analysis computing device 12 subtracts a value (e.g., 1, 2, or 3 mm) based on the observed data (MD-MedialFemoralCondyleWear) from the result of step 1102, or 1106 if performed, to obtain the femoral distal medial resection thickness (PL-FemoralMedialDistalResection). Referring back to step 1108, if the individualized kinematic knee replacement analysis computing device 12 determines that there is no medial femoral condyle bone wear on the coronal view, then the No branch is taken to step 1112. In step 1112, the process ends and the femoral distal medial resection thickness (PL-FemoralMedialDistalResection) is the result of step 1102, 1106, or 1110.

Figure 12:
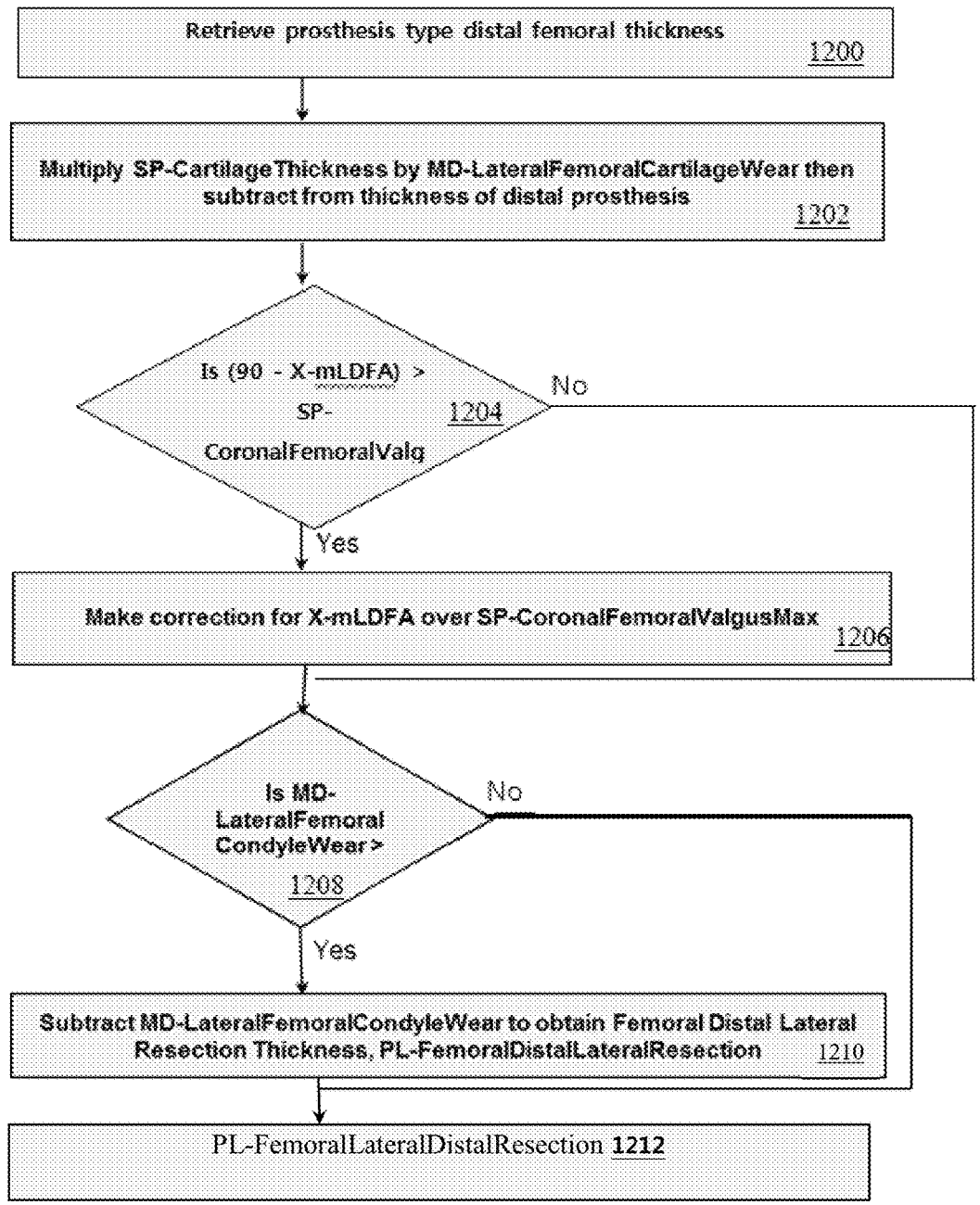
FIG. 12 is a flowchart of an exemplary method for generating a femoral distal lateral resection thickness for a specific patient.

Referring to FIG. 12, an exemplary method for generating a femoral distal lateral resection thickness (PL-FemoralLateralDistalResection) for a specific patient will now be described. In step 1200 in this example, the individualized kinematic knee replacement analysis computing device 12 retrieves a prosthesis type distal femoral thickness from the prosthesis table 42. In step 1202, the individualized kinematic knee replacement analysis computing device 12 multiplies cartilage thickness from the surgeon preference data (SP-Cartilage Thickness) by the percentage of lateral wear from the observed data (MD-LateralFemoralCartilageWear), and then subtracts from the thickness of the distal prosthesis.

Next, the individualized kinematic knee replacement analysis computing device 12 determines whether to accept the manufacturer's thickness of the prosthesis for femoral resection planning based on the surgeon preference data (SP-AdjustManufacturerDistalFemoralThickness). If the individualized kinematic knee replacement analysis computing device 12 determines that the manufacturer's thickness of the prosthesis should be accepted, then the distal lateral resection thickness (PL-FemoralLateralDistalResection) is not changed. However, if the individualized kinematic knee replacement analysis computing device 12 determines that the manufacturer's thickness of the prosthesis should not be accepted, then the distal lateral resection thickness (PL-FemoralLateralDistalResection) is modified by adding an amount determined based on the surgeon preference data (SP-DistalFemoralThicknessAdjustment).

In step 1204, the individualized kinematic knee replacement analysis computing device 12 determines whether 90 minus the coronal mLDFA (X-mLDFA) exceeds a threshold determined based on the surgeon preference data (SP-CoronalFemoralValgusMax). If the individualized kinematic knee replacement analysis computing device 12 determines that 90 minus the coronal mLDFA (X-mLDFA) exceeds the threshold, then the Yes branch is taken to step 1206. In step 1206, the individualized kinematic knee replacement analysis computing device 12 modifies the distal lateral resection thickness (PL-FemoralLateralDistalResection) by reducing the distal lateral resection thickness (PL-FemoralLateralDistalResection) by the difference of the actual lateral thickness and the corrected lateral thickness for less valgus than anatomically present.

Subsequent to making the correction in step 1206, or if the individualized kinematic knee replacement analysis computing device 12 determines in step 1204 that 90 minus the coronal mLDFA (X-mLDFA) does not exceeds the threshold and the No branch is taken, the individualized kinematic knee replacement analysis computing device 12 proceeds to step 1208. In step 1208 the individualized kinematic knee replacement analysis computing device 12 determines whether there is lateral femoral condyle bone wear on the coronal view based on the observed data (MD-MedialFemoralCondyleWear). If the individualized kinematic knee replacement analysis computing device 12 determines that there is medial femoral condyle bone wear on the coronal view, then the Yes branch is taken to step 1210.

In step 1210, the individualized kinematic knee replacement analysis computing device 12 subtracts a value (e.g., 1, 2, or 3 mm) based on the observed data (MD-MedialFemoralCondyleWear) from the result of step 1202, or 1206 if performed, to obtain the femoral distal lateral resection thickness (PL-FemoralLateralDistalResection). Referring back to step 1208, if the individualized kinematic knee replacement analysis computing device 12 determines that there is no lateral femoral condyle bone wear on the coronal view, then the No branch is taken to step 1212. In step 1212, the process ends and the femoral distal lateral resection thickness (PL-FemoralLateralDistalResection) is the result of step 1202, 1206, or 1210.

Figure 13:
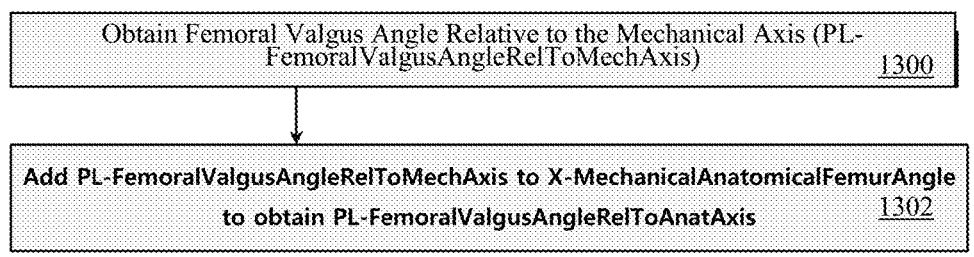
FIG. 13 is a flowchart of an exemplary method for generating a femoral valgus angle relative to an anatomic axis for a specific patient.

Referring to FIG. 13, an exemplary method for generating a femoral valgus angle relative to an anatomic axis (PL-FemoralValgusAngleRelativeToAnatomicAxis) for a specific patient will now be described. In step 1300 in this example, the individualized kinematic knee replacement analysis computing device 12 obtains the femoral valgus angle relative to the mechanical axis (PL-FemoralValgusAngleRelToMechAxis), generated as described and illustrated earlier with reference to FIG. 10. In step 1302, the individualized kinematic knee replacement analysis computing device 12 adds the femoral valgus angle relative to the mechanical axis (PL-FemoralValgusAngleRelToMechAxis) to the mechanical angle—anatomical angle of the femur (X-MechanicalAnatomicalFemurAngle) to obtain the Femoral Valgus Angle Relative to Anatomic Axis (PL-FemoralValgusAngleRelToAnatAxis).

Figure 14:
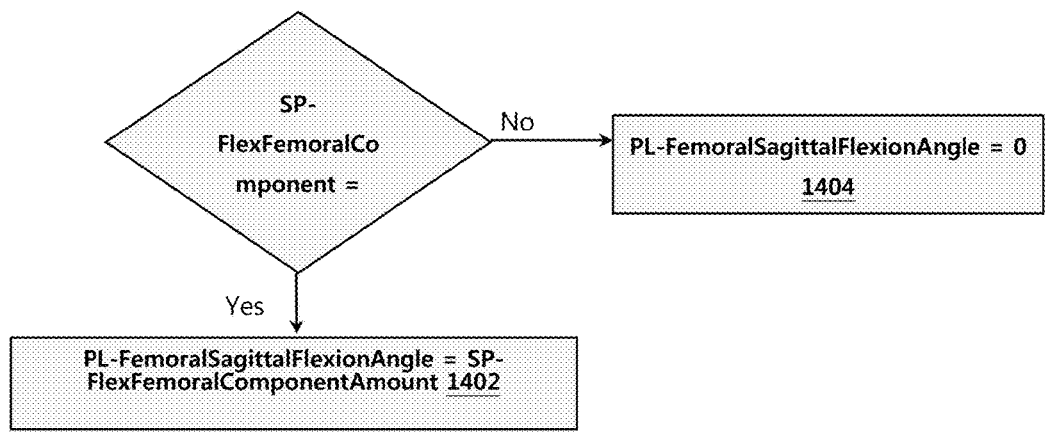
FIG. 14 is a flowchart of an exemplary method for determining a femoral sagittal flexion angle for a specific patient.

Referring to FIG. 14, an exemplary method for determining a femoral sagittal flexion angle (PL-FemoralSagittalFlexionAngle) for a specific patient will now be described. In step 1400 in this example, the individualized kinematic knee replacement analysis computing device 12 determines whether the femoral component should be flexed based on the surgeon preference data (SP-FlexFemoralComponent). If the individualized kinematic knee replacement analysis computing device 12 determines that the femoral component should be flexed, then the Yes branch is taken to step 1402.

In step 1402, the individualized kinematic knee replacement analysis computing device 12 sets the femoral sagittal flexion angle. (PL-FemoralSagittalFlexionAngle) based on the surgeon preference data (SP-FlexFemoralComponentAmount). Referring back to step 1400, if the individualized kinematic knee replacement analysis computing device 12 determines that the femoral component should not be flexed, then the No branch is taken to step 1404. In step 1404, the Individualized kinematic knee replacement analysis computing device 12 sets the femoral sagittal flexion angle (PL-FemoralSagittalFlexionAngle) to equal zero.

Figure 15:
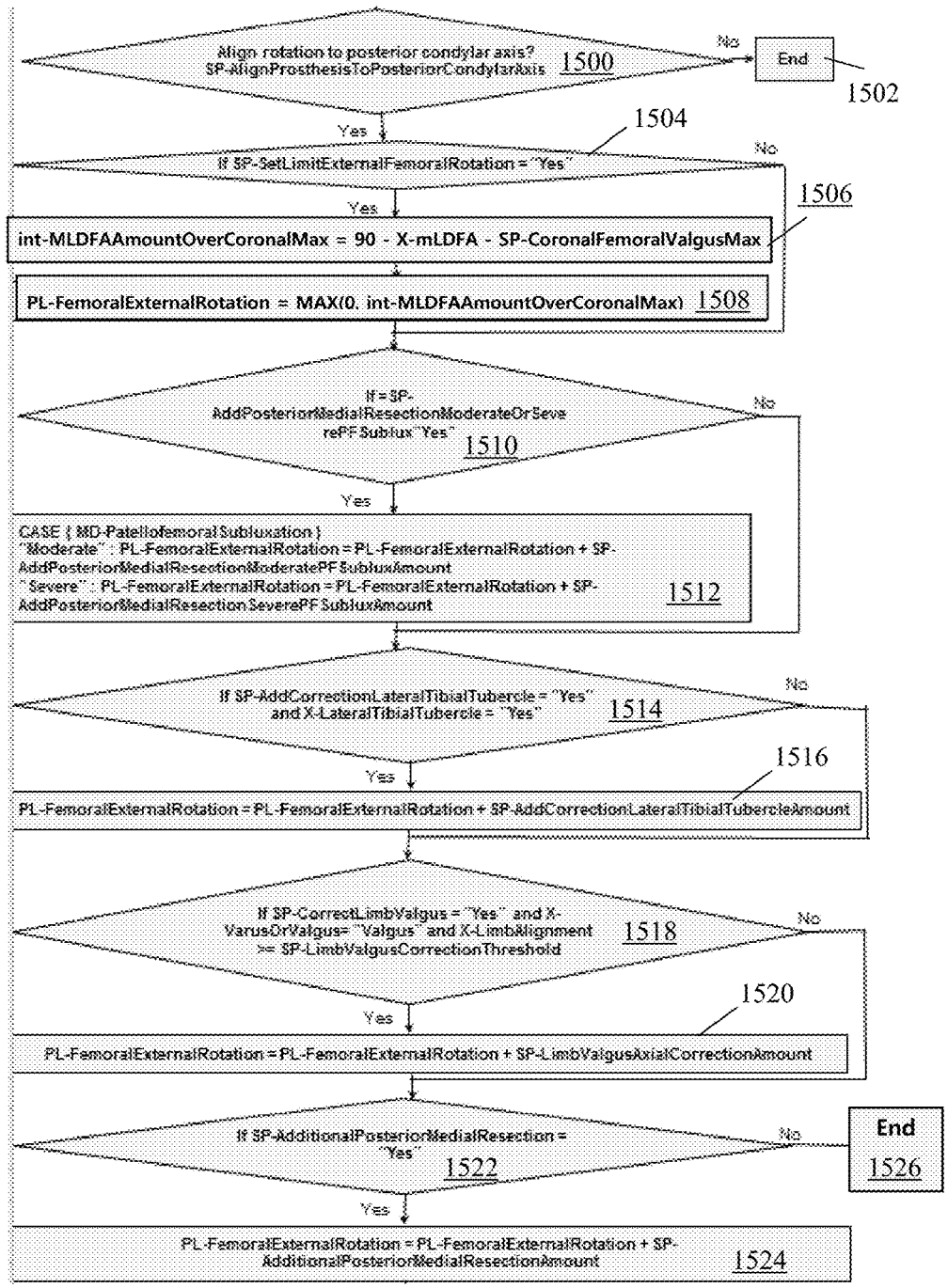
FIG. 15 is a flowchart of an exemplary method for generating a femoral external rotation angle for a specific patient.

Referring to FIG. 15, an exemplary method for generating a femoral external rotation angle (PL-FemoralExternalRotation) for a specific patient will now be described. In step 1500 in this example, the individualized kinematic knee replacement analysis computing device 12 determines whether the rotation is to be aligned to the posterior condylar axis based on the surgeon preference data (SP-AlignProsthesisToPosteriorCondylarAxis). If the individualized kinematic knee replacement analysis computing device 12 determines that the rotation is not aligned to the posterior condylar axis, then the No branch is taken to step 1502. In step 1502 the process ends and the femoral external rotation angle (PL-FemoralExternalRotation) is set to a default value (e.g., zero). Optionally, the individualized kinematic knee replacement analysis computing device 12 outputs a message to a display device informing the surgeon that mechanical alignment may be preferred for this patient, for example.

Referring back to step 1500, if the individualized kinematic knee replacement analysis computing device 12 determines that the rotation is to be aligned to the posterior condylar axis, then the Yes branch is taken to step 1504. In step 1504, the individualized kinematic knee replacement analysis computing device 12 determines whether a limit to the external femoral rotation has been set based on the surgeon preference data (SP-SetLimitExternalFemoralRotation). If the individualized kinematic knee replacement analysis computing device 12 determines that a limit to the external femoral rotation has been set, then the Yes branch is taken to step 1506. In one example, the individualized kinematic knee replacement analysis computing device 12 uses a translation of 1 mm resection equals 1 degree of femoral external rotation, however an alternative translation using a trigonometric computation based on patient anatomy or any other type of translation could also be used.

In step 1506, the individualized kinematic knee replacement analysis computing device 12 sets an intermediate value (Int-MLDFAAmountOverCoronalMax) equal to ninety minus the coronal mLDFA (X-mLDFA) minus the femoral coronal maximum value (SP-CoronalFemoralValgusMax) determined based on the surgeon preference data. In step 1508, the individualized kinematic knee replacement analysis computing device 12 sets the femoral external rotation angle (PL-FemoralExternalRotation) equal to the maximum of 0 and the intermediate value (Int-MLDFAAmountOverCoronalMax). Subsequent to setting the femoral external rotation angle (PL-FemoralExternalRotation) in step 1508, or if the individualized kinematic knee replacement analysis computing device 12 determines in step 1504 that a limit to the external femoral rotation has not been set and the No branch is taken, the individualized kinematic knee replacement analysis computing device 12 proceeds to step 1510.

In step 1510, the individualized kinematic knee replacement analysis computing device 12 determines whether additional resection should be added to the posterior medial cut for moderate patellofemoral subluxation based on the surgeon preference data (SP-AdditionalPosteriorMedialResection). If the individualized kinematic knee replacement analysis computing device determines that additional resection should be added to the posterior medial cut for moderate patellofemoral subluxation, then the Yes branch is taken to step 1512. In step 1512, the individualized kinematic knee replacement analysis computing device 12 modifies the femoral external rotation angle (PL-FemoralExternalRotation) according to the severity of the patellofemoral subluxation, which is determined based on the observed data (MD-Patellofemoral Subluxation).

Accordingly, in one example, the femoral external rotation angle (PL-FemoralExternalRotation) is incremented by an amount based on the surgeon preference data (SP-AddPosteriorMedialResectionModeratePFSubluxAmount or SP-AddPosteriorMedialResectionSeverePFSubluxAmount) that corresponds to the severity indicated in the observed data (MD-Patellofemoral Subluxation). Subsequent to modifying the femoral external rotation angle (PL-FemoralExternalRotation) in step 1512, or if the individualized kinematic knee replacement analysis computing device 12 determines in step 1510 that additional resection should not be added to the posterior medial cut for moderate patellofemoral subluxation and the No branch is taken, then the individualized kinematic knee replacement analysis computing device 12 proceeds to step 1514.

In step 1514, the individualized kinematic knee replacement analysis computing device 12 determines whether correction for lateral tibial tubercle should be added based on the surgeon preference data (SP-AddCorrectionLateralTibialTubercle) and whether there is lateral tibial tubercle for the specific patient based on the template data (X-LateralTibialTubercle). If the individualized kinematic knee replacement analysis computing device 12 determines that correction for lateral tibial tubercle should be added and that there is lateral tibial tubercle, then the Yes branch is taken to step 1516. In step 1516, the individualized kinematic knee replacement analysis computing device 12, modifies the femoral external rotation angle (PL-FemoralExternalRotation) by adding a correction amount for the lateral tibial tubercle based on the surgeon preference data (SP-AddCorrectionLateralTibialTubercleAmount). Subsequent to modifying the femoral external rotation angle (PL-FemoralExternalRotation) in step 1516, or if the individualized kinematic knee replacement analysis computing device 12 determines in step 1514 that correction for lateral tibial tubercle should not be added or there is not a lateral tibial tubercle for the specific patient and the No branch is taken, then the individualized kinematic knee replacement analysis computing device 12 proceeds to step 1518.

In step 1518, the individualized kinematic knee replacement analysis computing device 12 determines whether a correction should be made for limb valgus based on the surgeon preference data (SP-CorectLimbValgus), the limb for the specific patient is valgus based on the template data (X-VarusOrValgus), and the limb alignment determined based on the template data (X-LimbAlignment) is greater than or equal to a threshold value determined based on the surgeon preference data (SP-LimbValgusCorrectionThreshold). If the individualized kinematic knee replacement analysis computing device 12 determines that correction should be made for limb valgus, the limb is valgus, and the limb alignment is greater than or equal to the threshold value, then the Yes branch is taken to step 1520.

In step 1520, the individualized kinematic knee replacement analysis computing device 12 modifies the femoral external rotation angle (PL-FemoralExternalRotation) by adding a correction amount determined based on the surgeon preference data (SP-LimbValgusAxialCorrectionAmount). Subsequent to modifying the femoral external rotation angle (PL-FemoralExternalRotation), or if the individualized kinematic knee replacement analysis computing device 12 determines in step 1518 that a correction should not be made for limb valgus based on the surgeon preference data (SP-CorectLimbValgus), the limb for the specific patient is not valgus based on the template data (X-VarusOrValgus), or the limb alignment determined based on the template data (X-LimbAlignment) is not greater than or equal to a threshold value determined based on the surgeon preference data (SP-Limb ValgusCorrectionThreshold) and the No branch is taken, then the individualized kinematic knee replacement analysis computing device 12 proceeds to step 1522.

In step 1522, the individualized kinematic knee replacement analysis computing device 12 determines whether additional resection should be added to the medial posterior cut to avoid accidentally internally rotating the femur based on the surgeon preference data (SP-AdditionalPosteriorMedialResection). If the individualized kinematic knee replacement analysis computing device determines that additional resection should be added, then the Yes branch is taken to step 1524. In step 1524, the individualized kinematic knee replacement analysis computing device 12 modifies the femoral external rotation angle (PL-FemoralExternalRotation) by adding a posterior medial resection amount determines based on the surgeon preference data (SP-AdditionalPosteriorMedialResectionAmount). However, if the individualized kinematic knee replacement analysis computing device determines that additional resection should not be added, then the No branch is taken to step 1526 where the process ends.

Subsequent to step 1524 or 1526, the femoral external rotation angle (PL-FemoralExternalRotation) may include an angle greater than surgeon coronal femoral implant valgus maximum, the correction for patellofemoral subluxation, the correction for a lateral tibial tubercle, the amount of axial correction for limb valgus, and/or the external rotation addition to avoid internal rotation of the femur. Therefore, the femoral external rotation angle (PL-FemoralExternalRotation) is compared to surgeon preference data for maximum femoral external rotation (SP-ExternalFemoralRotationMax) and, if greater, the femoral external rotation (PL-FemoralExternalRotation) is set to the maximum femoral external rotation (PL-FemoralExternalRotationMax).

Figure 16:
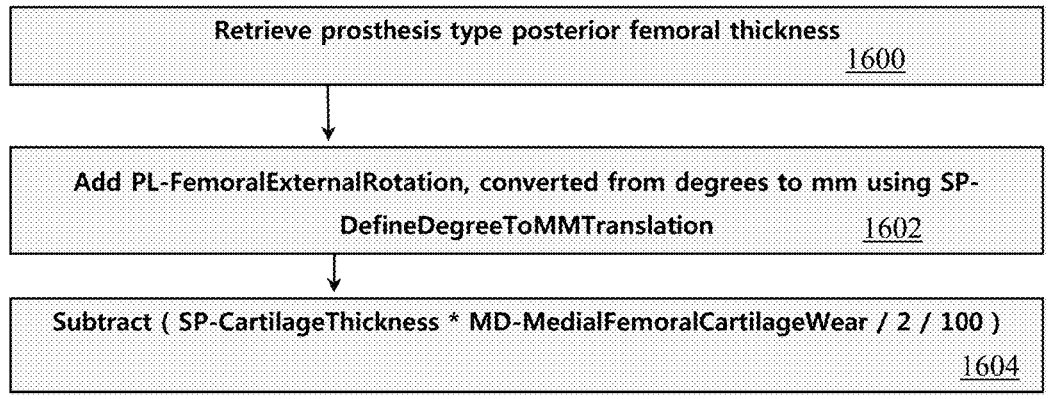
FIG. 16 is a flowchart of an exemplary method for generating a posterior medial resection thickness for a specific patient.

Referring to FIG. 16, an exemplary method for generating a posterior medial resection thickness (PL-FemoralPosteriorMedialResection) for a specific patient will now be described. In step 1600 in this example, the individualized kinematic knee replacement analysis computing device 12 retrieves a prosthesis type distal femoral thickness from the prosthesis table 42. In step 1602, the individualized kinematic knee replacement analysis computing device 12 adds the femoral external rotation (PL-FemoralExternalRotation), determined as described and illustrated earlier with reference to FIG. 15, to the retrieved prosthesis type distal femoral thickness. In this example, the individualized kinematic knee replacement analysis computing device 12 can convert the femoral external rotation (PL-FemoralExternalRotation) from degrees to millimeters, for example, using the surgeon preference data (SP-DefineDegreeToMMTranslation).

In step 1604, the individualized kinematic knee replacement analysis computing device 12 divides a medial femoral cartilage wear determined from the observed data (MD-MedialFemoralCartilageWear) by two and then by 100, multiplies the result by a cartilage thickness determined from the surgeon preference data (SP-CartilageThickness), and subtracts the result from the result of step 1602 to thereby generate the femoral posterior medial resection thickness (PL-FemoralPosteriorMedialResection).

Figure 17:
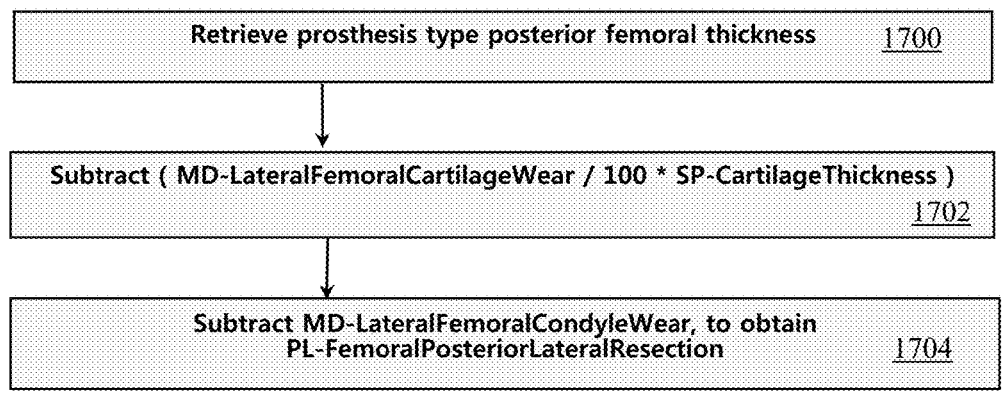
FIG. 17 is a flowchart of an exemplary method for generating a posterior lateral resection thickness for a specific patient.

Referring to FIG. 17, an exemplary method for generating a posterior lateral resection thickness (PL-FemoralPosteriorLateralResection) for a specific patient will now be described. In step 1700 in this example, the individualized kinematic knee replacement analysis computing device 12 retrieves a prosthesis type distal femoral thickness from the prosthesis table 42. In step 1702, the individualized kinematic knee replacement analysis computing device 12 divides the lateral femoral cartilage wear determined based on the observed data (MD-LateralFemoralCartilageWear) by 100 and multiplies the result by a cartilage thickness determined from the surgeon preference data (SP-CartilageThickness). In step 1704, the individualized kinematic knee replacement analysis computing device 12 subtracts any lateral femoral condyle bone wear on the coronal view determines from the observed data (MD-LateralFemoralCondyleWear) from the result of step 1702 to thereby generate the posterior lateral resection thickness (PL-FemoralPosteriorLateralResection).

Figure 18:
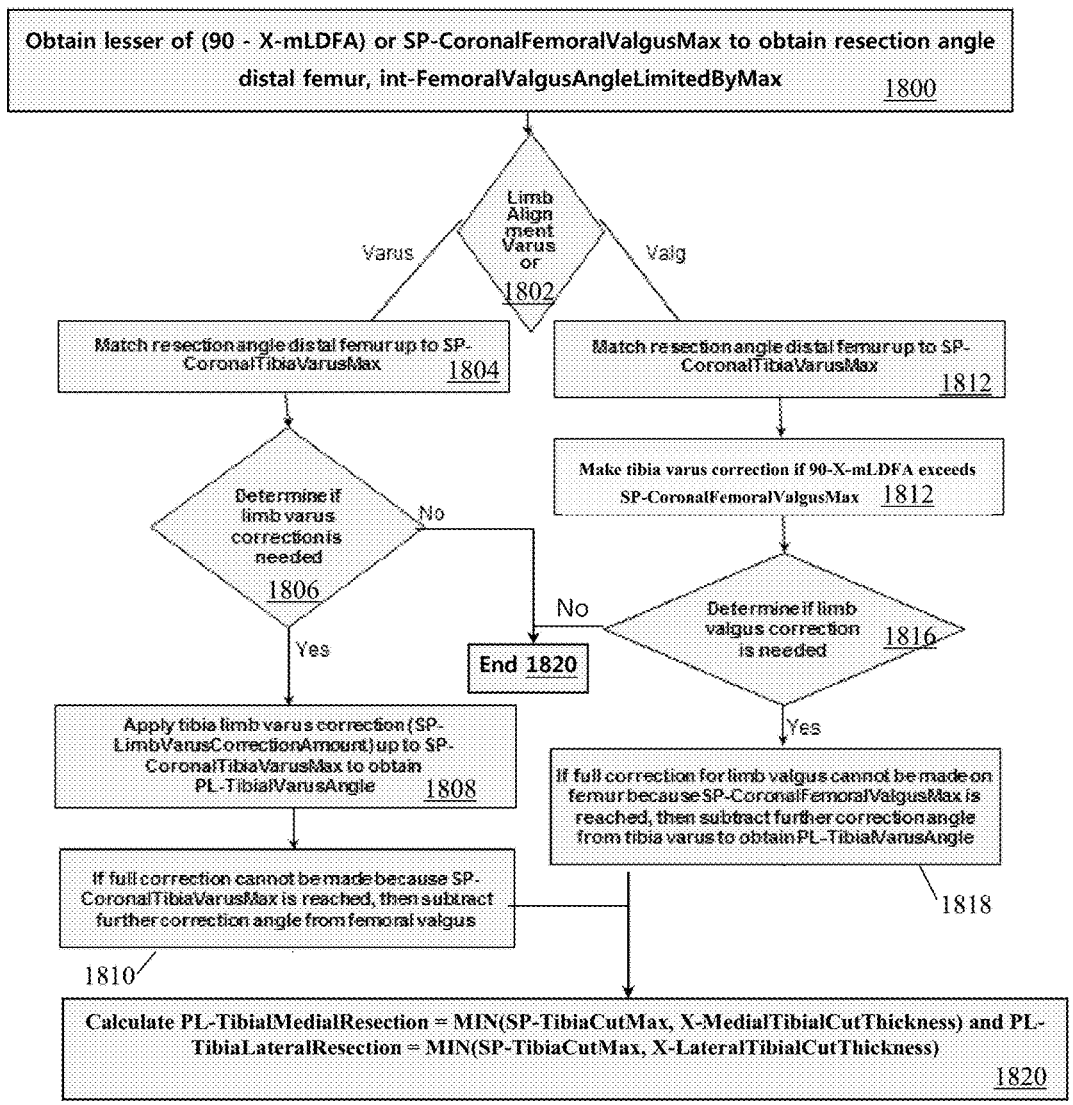
FIG. 18 is a flowchart of an exemplary method for determining a tibial resection angle, tibial medial and lateral resection thicknesses, and a slope for a specific patient.

Referring to FIG. 18, an exemplary method for determining a tibial resection angle (PL-TibialVarusAngle), tibial medial (PL-TibialMedialResection), and lateral (PL-Tibial- LateralResection) resection thicknesses, and a slope (PL-TibialSlope) for a specific patient will now be described. In step 1800 in this example, the individualized kinematic knee replacement analysis computing device 12 sets an intermedia femoral resection valgus angle (int-FemoralValgusAngleLimitedByMax) equal to the lesser of the coronal mLDFA determined from the template data (X-mLDFA) or a coronal femoral valgus maximum determined from the surgeon preference data (SP-CoronalFemoralValgusMax).

In step 1802, the individualized kinematic knee replacement analysis computing device 12 determines whether the surgeon would like to make a correction for the limb being varus or valgus based on the surgeon preference data (SP-CorrectLimbVarus). If the individualized kinematic knee replacement analysis computing device 12 determines that the surgeon would like to make a correction for the limb being varus, then the varus branch is taken to step 1804. In step 1804, the individualized kinematic knee replacement analysis computing device 12 matches the femoral resection valgus angle (int-FemoralValgusAngleLimitedByMax) to the tibial varus angle up to the surgeon designated maximum determined from the surgeon preference data (SP-CoronalTibiaVarusMax).

In step 1806, the individualized kinematic knee replacement analysis computing device 12 determines whether the limb is equal to or greater than the amount of varus which will threshold a correction by comparing the long leg xray coronal HKA determined from the template data (X-LimbAlignment) to the angle which thresholds a correction determined from the surgeon preference data (SP-LimbVarusCorrectionThreshold). If the individualized kinematic knee replacement analysis computing device 12 determines that the limb is equal to or greater than the amount of varus which will threshold a correction, then the Yes branch is taken to step 1808.

In step 1808, the individualized kinematic knee replacement analysis computing device 12 applies a tibia limb varus correction determined from the surgeon preference data (SP-LimbVarusCoreectionAmount) up to a surgeon specified maximum tibial varus (SPCoronalTibiaVarusMax) to obtain the tibial resection angle (PL-TibialVarusAngle). In step 1810, the individualized kinematic knee replacement analysis computing device 12 subtracts a further correction angle from femoral valgus, such as the excess correction (int-ExcessVarusLimbCorrection) determined as described and illustrated in more detail earlier with reference to step 1006 of FIG. 10, when the individualized kinematic knee replacement analysis computing device 12 determines the full correction cannot be made in step 1808 because the tibial varus maximum (SP-CoronalTibiaVarusMax) is reached.

Referring back to step 1802, if the limb is in valgus (X-VarusOrValgus), then the valgus branch is taken to step 1812. In step 1812, the individualized kinematic knee replacement analysis computing device 12 matches the femoral resection valgus angle (int-FemoralValgusAngleLimitedByMax) to the tibial varus angle up to the surgeon designated maximum determined from the surgeon preference data (SP-CoronalTibiaVarusMax). In step 1814, the individualized kinematic knee replacement analysis computing device 12 makes a tibia varus correction if 90 minus the coronal mLDFA (X-mLDFA) exceeds a coronal femoral valgus maximum determined from the surgeon preference data (SP-CoronalFemoralValgusMax). In order to make the tibia varus correction, the individualized kinematic knee replacement analysis computing device applies an intermediate excess valgus limb correction (int-ExcessValgusLimbCorrection) to the tibia by subtracting the excess correction from the intermediate femoral valgus angle limited by maximum (int-FemoralValgusAngleLimitedByMax) obtained in step 1800.

In step 1816, the individualized kinematic knee replacement analysis computing device 12 determines whether limb valgus correction is needed based on the surgeon preference (SP-CorrectLimbValgus), the surgeon preferred threshold for correction (SP-LimbValgusCorrectionThreshold) and the surgeon preferred amount of correction (SP-LimbValgusCoronalCorrectionAmount. If the \individualized kinematic knee replacement analysis computing device 12 determines that limb valgus correction is needed, then the Yes branch is taken to step 1818. In step 1818, the individualized kinematic knee replacement analysis computing device subtracts a further correction angle from the tibia varus resulting in the tibial varus angle (PL-TibialVarusAngle), when the individualized kinematic knee replacement analysis computing device 12 determines the full correction cannot be made on the femur because the coronal femoral valgus maximum (SP-CoronalFemoralValgusMax) is reached. If the individualized kinematic knee replacement analysis computing device 12 determines in step 1706 that the limb is not equal to or greater than the amount of varus which will threshold a correction, or in step 1716 that limb valgus correction is not needed, then the respective No branch is taken and the method ends in step 1820.

With the tibial resection angle (PL-TibialVarusAngle), a surgeon can template a long-leg X-Ray for medial and lateral tibial resections up to the surgeon preferred maximum tibial resection, which is determined based on the surgeon preference data (SP-TibiaResectionMax). Thereby, the surgeon can obtain additional template data (X-MedialTibialResectionThickness and X-LateralTibialResectionThickness) corresponding to a portion of the recommended three-dimensional knee replacement surgeon plan (PL-TibialMedialResection and PL-TibialLateralResection, respectively). Additionally, the surgeon can use the manufacturer's recommended or templated tibial slope, or surgeon-preferred maximum over the manufacturer's recommended tibial slope. Optionally, the surgeon can float the tibial trial to match the femoral rotation (self-seeking method), or use any other method in order to determine the tibial rotation Referring to FIG. 19, a flowchart of an exemplary method for updating default recommended preference data based on historical outcome data is illustrated. In step 1900 in this example, the learning module 44 of the individualized kinematic knee replacement analysis computing device 12 obtains historical outcome data and associated recommended three-dimensional knee replacement surgeon plans from the outcome database 22, as well as, optionally, associated demographic data. The outcome data, recommended three-dimensional knee replacement surgeon plans, and/or demographic data could have been stored in the outcome database 22 as described and illustrated earlier with reference to step 518 of FIG. 3, for example, although the outcome data and/or recommended three-dimensional knee replacement surgeon plans could have been stored in other manners in other examples. In some examples, the outcome data includes range of motion data, one or more outcome scores, patient satisfaction data, or reoperation data, although other types of outcome data can also be used.

In step 1902, the learning module 44 of the individualized kinematic knee replacement analysis computing device 12 performs a statistical analysis on the data obtained in step 1900. The statistical analysis can be based on a correlation of the outcome data with the recommended three-dimensional knee replacement surgeon plans and, optionally, the demographic data, to determine portions of the recommended three-dimensional knee replacement surgeon plans that resulted in improved outcomes for patients sharing one or more characteristics (e.g., anatomic or demographic characteristics).

In step 1904, the learning module 44 of the individualized kinematic knee replacement analysis computing device 12 updates default or recommended preference data that is stored in the memory 28 and used by the surgeon plan module 34 when obtaining preference data, as described and illustrated earlier with reference to step 500 of FIG. 5. Accordingly, recommended preference data that results in recommended three-dimensional knee replacement surgeon plans for patients that, when implemented, lead to improved outcomes can be modified over time. While the recommended preference data can be modified by each surgeon during each iteration of steps 500-518 for individual patients, the recommended preference data can inform the decisions made by surgeons for certain portions of the preference data ultimately obtained and used by the surgeon plan module 34 as described and illustrated earlier.

In some examples, steps 1900-1904 are performed periodically by the individualized kinematic knee replacement analysis computing device 12, although an administrator can also manually initiate the learning module 44 in other examples. Optionally, subsequent ones of the surgeon interface(s) 36 provided to the surgeon client computing device 14 can include an indication of the default or recommended preference data for use by a surgeon, as well as an indication that a subset of the default or recommended preference data has been updated.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A non-transitory computer readable medium having stored thereon instructions for facilitating individualized kinematically aligned knee replacements comprising executable code which when executed by one or more hardware processors, causes the one or more hardware processors to:
obtain prosthesis data for a selected prosthesis;
generate anatomical and pathoanatomical data for a specific patient, wherein the anatomical data comprises at least a coronal mechanical lateral distal femoral angle that is specific to the patient;
generate bone and cartilage resection data based at least in part on the prosthesis data, the anatomical data, and the pathoanatomical data; and
output a recommended three-dimensional knee replacement surgeon plan for the patient comprising the bone and cartilage resection data for facilitating implantation of the prosthesis in the patient.

2. The non-transitory computer readable medium as set forth in claim 1, wherein the anatomical data further comprises a posterior condylar axis that is specific to the patient.

3. The non-transitory computer readable medium as set forth in claim 1, wherein the bone and cartilage resection data comprises one or more femoral component coronal alignment angles, one or more femoral distal thicknesses, a femoral component axial external rotation angle, one or more femoral posterior resection thicknesses, a tibial component coronal alignment angle relative to the coronal mechanical axis of a tibia of the patient, one or more tibia resection thicknesses, and a tibia sagittal slope.

4. The non-transitory computer readable medium as set forth in claim 1, wherein the executed code, when executed by the one or more hardware processors, further causes the one or more hardware processors to:
perform a statistical analysis on outcome data retrieved from a database, the outcome data comprising demographic information for a plurality of other patients and one or more of range of motion data, one or more outcome scores, patient satisfaction data, or reoperation data for one or more of the other patients; and
generate default preference data for the patient based at least in part on the statistical analysis, wherein the bone and cartilage resection data is further generated based at least in part on the default preference data.

5. The non-transitory computer readable medium as set forth in claim 1, wherein the executed code, when executed by the one or more hardware processors, further causes the one or more hardware processors to obtain preference data and observed data for a patient, wherein the bone and cartilage resection data is further generated based on the preference data and the observed data and the preference data limits an alignment of the prosthesis and a limb of the patient to within a predetermined number of degrees of a mechanical axis of a femur, tibia, or limb of the patient.

6. The non-transitory computer readable medium as set forth in claim 1, wherein the executed code, when executed by the one or more hardware processors, further causes the one or more hardware processors to facilitate the generation of one or more individualized knee replacement guides according to the recommended three-dimensional knee replacement surgeon plan.

7. An individualized kinematic knee replacement analysis computing device comprising memory comprising programmed instructions and one or more processors coupled to the memory and configured to be capable of executing the programmed instructions stored in the memory to:
obtain prosthesis data for a selected prosthesis;
generate anatomical and pathoanatomical data for a specific patient, wherein the anatomical data comprises at least a coronal mechanical lateral distal femoral angle that is specific to the patient;
generate bone and cartilage resection data based at least in part on the prosthesis data, the anatomical data, and the pathoanatomical data; and
output a recommended three-dimensional knee replacement surgeon plan for the patient comprising the bone and cartilage resection data for facilitating implantation of the prosthesis in the patient.

8. The individualized kinematic knee replacement analysis computing device as set forth in claim 7, wherein the anatomical data further comprises a posterior condylar axis that is specific to the patient.

9. The individualized kinematic knee replacement analysis computing device as set forth in claim 7, wherein the bone and cartilage resection data comprises one or more femoral component coronal alignment angles, one or more femoral distal thicknesses, a femoral component axial external rotation angle, one or more femoral posterior resection thicknesses, a tibial component coronal alignment angle relative to the coronal mechanical axis of a tibia of the patient, one or more tibia resection thicknesses, and a tibia sagittal slope.

10. The individualized kinematic knee replacement analysis computing device as set forth in claim 7, wherein the one or more processors are further configured to be capable of executing the programmed instructions stored in the memory to:
   perform a statistical analysis on outcome data retrieved from a database, the outcome data comprising demographic information for a plurality of other patients and one or more of range of motion data, one or more outcome scores, patient satisfaction data, or reoperation data for one or more of the other patients; and
   generate default preference data for the patient based at least in part on the statistical analysis, wherein the bone and cartilage resection data is further generated based at least in part on the default preference data.

11. The individualized kinematic knee replacement analysis computing device as set forth in claim 7, wherein the one or more processors are further configured to be capable of executing the programmed instructions stored in the memory to obtain preference data and observed data for a patient, wherein the bone and cartilage resection data is further generated based on the preference data and the observed data and the preference data limits an alignment of the prosthesis and a limb of the patient to within a predetermined number of degrees of a mechanical axis of a femur, tibia, or limb of the patient.

12. The individualized kinematic knee replacement analysis computing device as set forth in claim 7, wherein the one or more processors are further configured to be capable of executing the programmed instructions stored in the memory to facilitate the generation of one or more individualized knee replacement guides according to the recommended three-dimensional knee replacement surgeon plan.

* * * * *